(12) United States Patent
Hamill

(10) Patent No.: US 11,154,268 B2
(45) Date of Patent: Oct. 26, 2021

(54) HIGH-RESOLUTION ANTI-PINHOLE PET SCAN

(71) Applicant: Siemens Medical Solutions USA, Inc., Malvern, PA (US)

(72) Inventor: James J. Hamill, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 390 days.

(21) Appl. No.: 16/284,222

(22) Filed: Feb. 25, 2019

(65) Prior Publication Data

US 2019/0282193 A1 Sep. 19, 2019

Related U.S. Application Data

(60) Provisional application No. 62/644,648, filed on Mar. 19, 2018.

(51) Int. Cl.
*A61B 6/00* (2006.01)
*G01T 1/29* (2006.01)
*A61B 6/03* (2006.01)

(52) U.S. Cl.
CPC ............ *A61B 6/5235* (2013.01); *A61B 6/032* (2013.01); *A61B 6/037* (2013.01); *G01T 1/2985* (2013.01)

(58) Field of Classification Search
CPC ....... A61B 6/5235; A61B 6/032; A61B 6/037; A61B 6/4291; A61B 6/5205; A61B 6/465; A61B 6/463; A61B 6/488; G01T 1/2985; G01T 1/1648; G01T 1/1611
See application file for complete search history.

(56) References Cited

U.S. PATENT DOCUMENTS

| | | | |
|---|---|---|---|
| 2005/0008126 A1* | 1/2005 | Juh | A61B 6/037 378/207 |
| 2008/0111081 A1 | 5/2008 | Chuang | |
| 2008/0269594 A1* | 10/2008 | Paul | G01R 33/481 600/411 |
| 2016/0195624 A1* | 7/2016 | DiFilippo | G01T 1/2985 250/362 |
| 2021/0056688 A1* | 2/2021 | Xu | G06K 9/3241 |

* cited by examiner

*Primary Examiner* — Michael C Bryant

(57) ABSTRACT

The present disclosure relates to a new positron emission tomography (PET) scanning method that generates images with improved spatial resolution. The method includes placing a plurality of radiation-attenuating rods in a parallel arrangement near the target region of a patient, where the rods are in a first orientation with respect to the patient and conducting one or more PET scans of the target region generating a projection data that includes the radiation-attenuating rods, and reconstructing an image of the target region from the projection data.

28 Claims, 28 Drawing Sheets

120
FIG. 3C
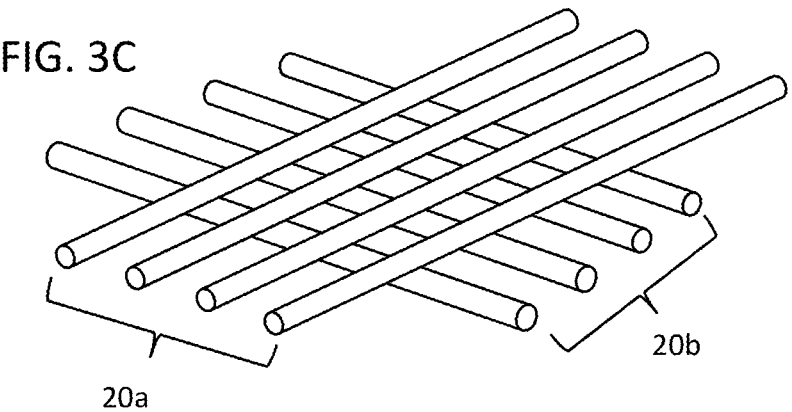
20a  20b
130
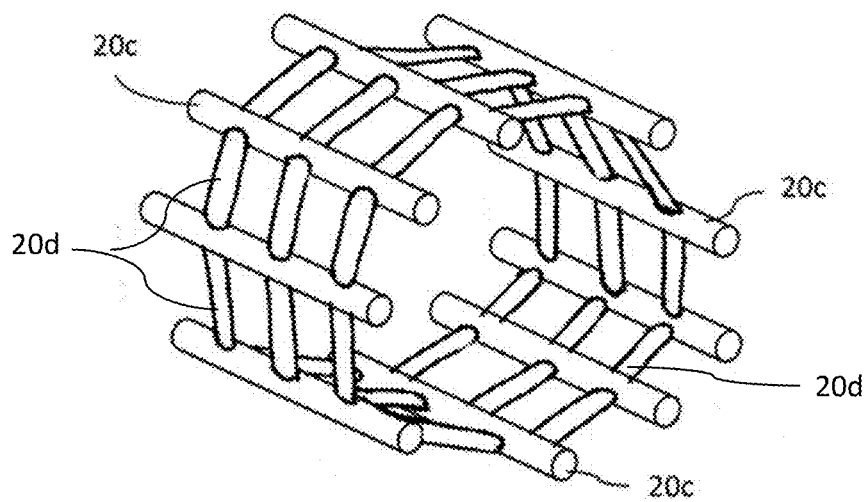
20c  20d
FIG. 3D

|     | H1 | H2 | H3 | H4 | H5 | H6 | H7 | H8 | H9 | H10 |
|-----|----|----|----|----|----|----|----|----|----|----|
| V1  |    |    |    |    |    |    |    |    |    |    |
| V2  |    |    |    |    |    |    |    |    |    |    |
| V3  |    |    |    |    |    |    |    |    |    |    |
| V4  |    |    |    |    |    |    |    |    |    |    |
| V5  |    |    |    |    |    |    |    |    |    |    |
|     |    |    | C1 | C2 | C3 | C4 |    | C5 |    |    |
| V6  |    |    |    |    |    |    |    |    |    |    |
| V7  |    |    |    |    |    |    |    |    |    |    |
| V8  |    |    |    |    |    |    |    |    |    |    |
| V9  |    |    |    |    |    |    |    |    |    |    |
| V10 |    |    |    |    |    |    |    |    |    |    |

FIG. 12

HIGH-RESOLUTION ANTI-PINHOLE PET SCAN

CROSS-REFERENCE TO RELATED APPLICATIONS

This application claims priority under 35 U.S.C. § 119(e) to U.S. Provisional Application No. 62/644,648, filed Mar. 19, 2018, the entire contents of which are incorporated herein by reference.

FIELD

This disclosure is generally related to positron emission tomography (PET) imaging, and more specifically to systems and methods that can improve the spatial resolution of clinical PET scanners.

BACKGROUND

Positron emission tomography (PET) is a modality of nuclear medicine for imaging metabolic processes by employing gamma photons emanated from radiopharmaceuticals ingested by a patient or injected into a patient.

One of the down sides of clinical PET scanners is that the scanners' spatial resolution is too coarse to resolve accurate images of targets or regions of interest that are smaller than the spatial resolution of the PET scanner. Some examples of such targets are prostate, lymph nodes, and the fine structures in the brain. Therefore, there is a need for improving the spatial resolution of PET scanners. In nuclear medicine, the most common method for overcoming fundamental resolution limitations is to use magnifying collimation with electronic or mechanical approach. Although this is common in single-photon nuclear medicine, it is rarely done in PET.

SUMMARY

The present disclosure relates to a new PET scanning method that generates images with improved spatial resolution. The method includes placing a plurality of radiation-attenuating rods in a parallel arrangement near the target region of a patient, wherein the radiation-attenuating rods are in a first orientation with respect to the patient, and conducting one or more PET scans of the target region, thus generating a projection data that includes the radiation-attenuating rods, and reconstructing a PET scan image of the target region from the projection data. The plurality of radiation attenuating rods in a parallel arrangement placed near the target region effectively produces a collimation effect enhancing the spatial resolution of the PET scan image similar to the pin-hole collimators but with improved image quality and collimation hardware that is easier to handle.

In some embodiments, after conducting the one or more PET scans of the target region to generate the projection data, the plurality of radiation-attenuating rods are re-oriented to a second orientation with respect to the patient, and a second set of one or more PET scans are conducted to generate a second projection data. Then, a PET scan image of the target region is reconstructed from the two projection data.

In some embodiments, a non-transitory, machine-readable storage medium encoded with program instructions for controlling a PET scanner is disclosed. When a processor executes the program instructions, the processor performs the method for self-TA for a PET scanner as disclosed herein.

BRIEF DESCRIPTION OF THE DRAWINGS

FIG. 3C is a schematic illustration of a plurality of radiation-attenuating rods in an alternate arrangement for providing anti-pinhole collimation in PET scan according to another embodiment of the present disclosure.

FIG. 3D is a schematic illustration of a plurality of radiation-attenuating rods in an additional alternate arrangement for providing anti-pinhole collimation in PET scan according to another embodiment of the present disclosure.

FIG. 12 shows a grid of x-y positions for the five $^{68}$Ge rods and twenty tungsten rods used in the experiments.

DETAILED DESCRIPTION

This description of the exemplary embodiments is intended to be read in connection with the accompanying drawings, which are to be considered part of the entire written description.

Figure 1A:
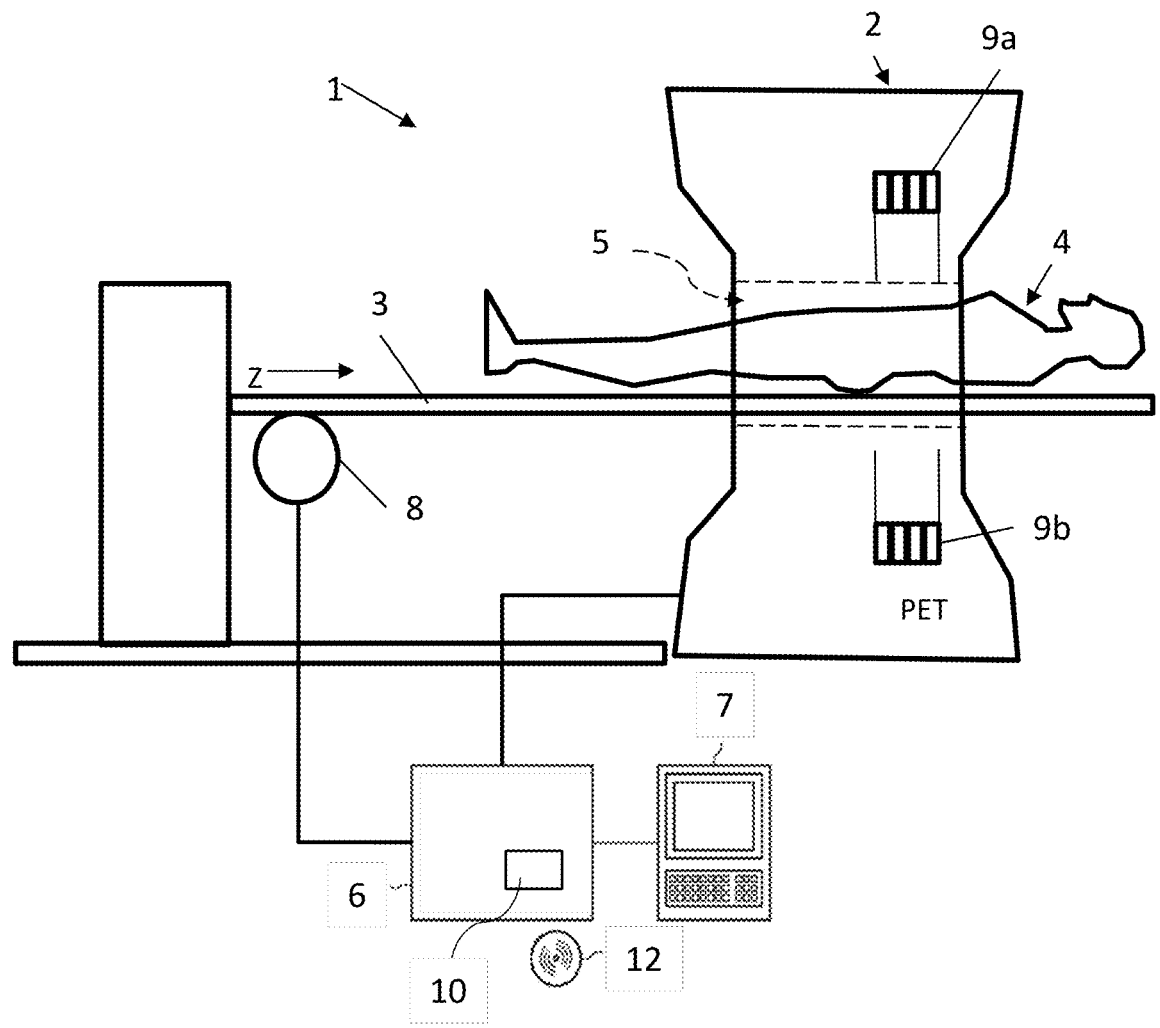
FIG. 1A is a high-level block diagram of a PET scanner system.

FIG. 1A is a high-level schematic diagram of a PET scanner system 1 in accordance with an embodiment of the present disclosure. In some embodiments, the PET scanner system 1 includes a PET scanner 2, one or more rings of PET detector blocks 9a, 9b (3D coincidence detectors) for detecting the gamma photons from the scan target region in the patient 4. The PET scanner system 1 comprises: a patient bed 3 for the patient 4 who can be moved on the patient bed 3 through an opening 5 of the PET scanner 2, a data processing and control unit 6, a display unit 7 and a drive unit 8.

In general, a patient is injected with a short-lived radioactive tracer isotope (e.g., usually into blood circulation) before conducting a PET scan. As the tracer-concentrated tissue in the patient undergoes positron emission decay, the tissue emits positrons, which are antiparticles of electrons with opposite charge. The positrons eventually collide with electrons in close vicinity of the tracer-concentrated tissue, each positron producing a pair of annihilation (gamma) photons moving in opposite directions that are received and detected by the detector blocks 9a, 9b.

The a data processing and control unit 6 is operable to receive signals from the PET detector blocks 9a, 9b, conduct coincidence processing, generate useable sinogram data, reorganize the sinogram data into projection data, and perform image reconstruction to generate PET scan images. The a data processing and control unit 6 processes the signals from the PET detector blocks 9a, 9b, representing the detected pairs of gamma photons that originated from coincidence events in the target region, into projection data and performs mathematical image reconstruction algorithms and generate the final PET scan images. The PET scan images can be shown on the display unit 7.

The a data processing and control unit 6 can further activate the drive unit 8 in order to move the patient bed 3 in a direction Z together with the patient 4 through the opening 5 of the PET scanner 2. The a data processing and control unit 6 and the processor 7 can, for example, comprise a computer system with a screen, a keyboard and a non-transitory, machine readable storage medium 12 (hereinafter, "storage medium") on which electronically-readable control information is stored, which is embodied so that it carries out the method described below when the storage medium 12 is used in conjunction with the processor 7 and the a data processing and control unit 6.

According to the present disclosure, high spatial image resolution in PET scan is achieved using anti-pinhole collimation concept, avoiding some of the disadvantages of existing pinhole collimation technology such as those exemplified in U.S. Pat. No. 10,078,144. Whereas pinhole collimation uses a massive collimator to block all radiation except in pinholes, thus reducing the number of detected coincidence events, the anti-pinhole collimation concept of the present disclosure places a plurality of gamma photon radiation-attenuating rods in a parallel arrangement in place of the pinhole collimators. The arrangement of radiation-attenuating rods present a smaller mass of radiation-attenuating material between the gamma photon source and the detectors. Accordingly, the anti-pinhole collimation of the present disclosure generates improved PET scan images compared to the existing pinhole collimation PET scan methods because instead of only the radiation that penetrates through the pinholes arriving at the detectors, all radiation reaches the detectors except for the small amount absorbed by the anti-pinholes (the radiation-attenuating rods). Additionally, the anti-pinhole collimation units are lighter than the existing pinhole collimators because the anti-pinhole units require less gamma photon absorbing material.

Figure 1B:
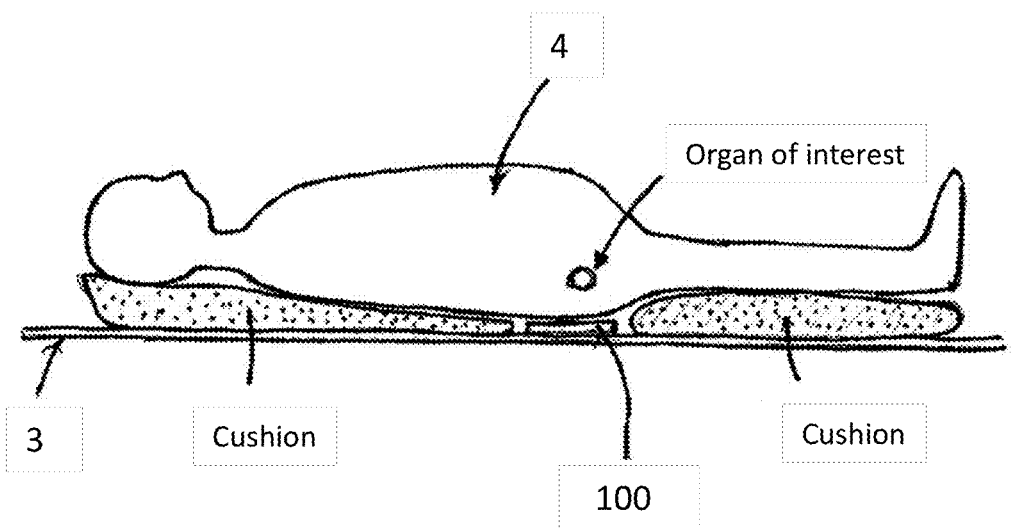
FIG. 1B is a schematic illustration of an example of a placement of a set of a plurality of radiation-attenuating rods in relation to a patient in a PET scanner according to the present disclosure.

FIG. 1B shows a schematic illustration of a patient 4 lying on a patient bed 3 in the PET scanner showing an example of a placement of a housing 100 holding a set of a plurality of radiation-attenuating rods in relation to the organ of interest to be PET scanned according to the present disclosure.

Figure 2:
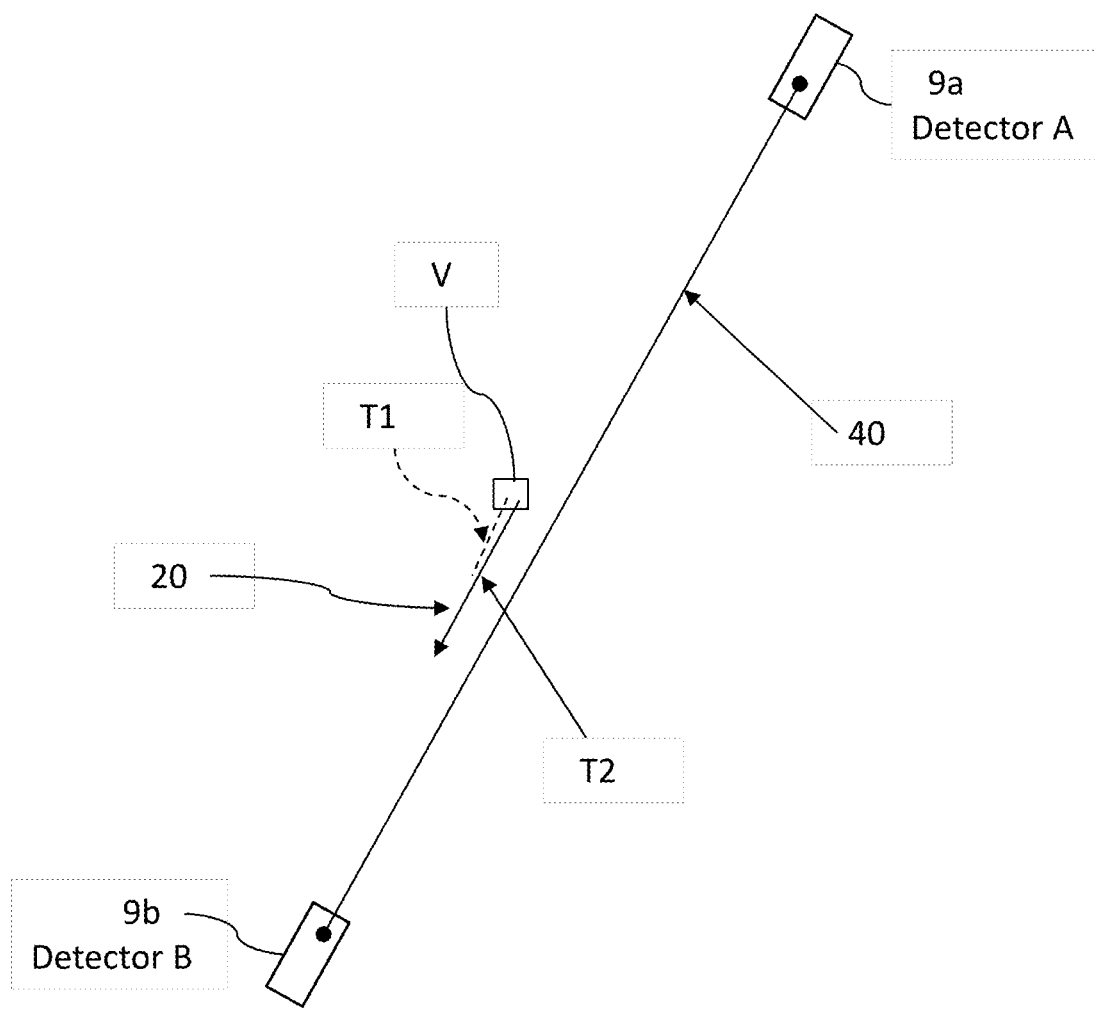
FIG. 2 is a schematic illustration of a pair of PET detectors a radiation emitting voxel and a radiation-attenuating rod as an anti-pinhole.

FIG. 2 shows a schematic illustration of the relationship between radiation-attenuating rods 20 and a PET detector showing the concept of anti-pinhole collimation. A radiation emitting voxel V (in the region of interest in the patient), a radiation-attenuating rod 20 (also referred to herein as an "anti-pinhole") are shown in relation to a pair of opposing PET detectors Detector A 9a and Detector B 9b. A line of response (LOR) 40 is drawn between the two detectors. Even though the voxel V is not directly between the detectors A and B (9a and 9b), radiation from the voxel is nevertheless seen by the A-B pair because, sometimes, annihilation radiation photons are not emitted in perfectly 180 degrees opposing directions. This effect is the origin of the image blurring due to the so-called non-collinearity effect, and it is a type of blurring that can be overcome by the use of pinhole or anti-pinhole collimation. The anti-pinhole 20 is placed close to the radiation emitting voxel V and the location of the anti-pinhole 20 is known. When a pair of photons from the radiation emitting voxel V is detected and we know that either the A photon (the photon detected by Detector A) or B photon (the photon detected by Detector B) is directed through an anti-pinhole, we reduce the detector tube's size, i.e., the measurement has the potential for higher spatial resolution. "Detector tube" refers to a conceptual tube that connects the Detector A and Detector B in the image space. Although the actual path of the emitted photon from the voxel V is trajectory T1, taking into consideration the non-collinearity of the pair of photons emitted from the voxel V during PET scan, the reconstruction algorithms will back project the measured data in the sinograms along lines through the anti-pinhole 20 along trajectory T2. The trajectory T2 passes through the center of the anti-pinhole 20 and is parallel to the LOR 40 and is an excellent approximation for voxels that are close to the anti-pinhole 20.

Unlike in the conventional pinhole collimation PET imaging where only the gamma radiation from the emitting voxels that pass through the pinholes in the collimator reach the PET detectors, the anti-pinhole collimation PET uses shadow-casting cylinders or rods made of a radiation attenuating material that are in parallel arrangement to effectuate a one-dimensional collimation with high sensitivity.

Figure 3A:
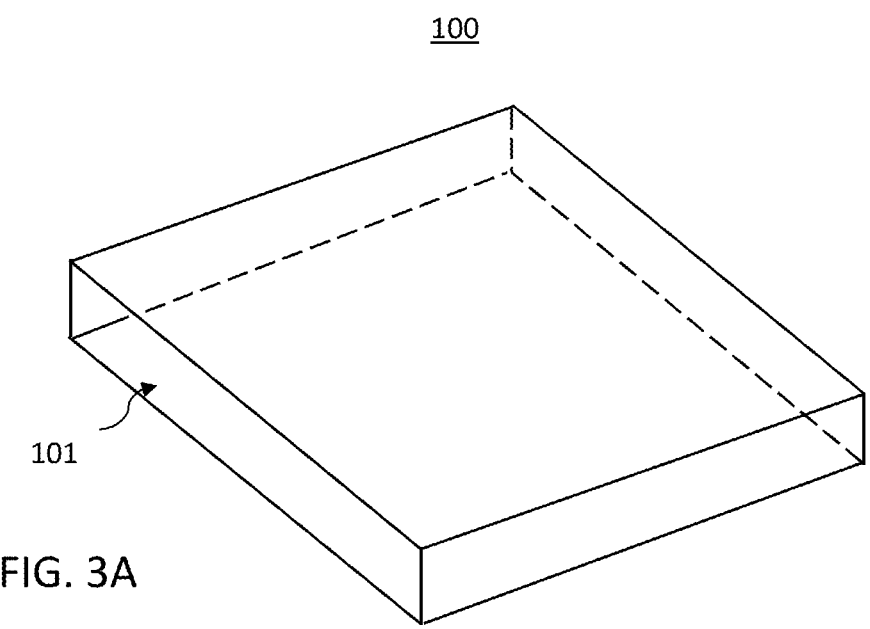
FIG. 3A is a schematic illustration of a housing for a plurality of radiation-attenuating rods according to an embodiment of the present disclosure.

FIG. 3A shows a schematic illustration of an example of the housing 100 for a plurality of radiation-attenuating rods according to an embodiment of the present disclosure. In the illustrated example, the housing 100 has an opening 101 for receiving a set of a plurality of radiation-attenuating rods.

Figure 3B:
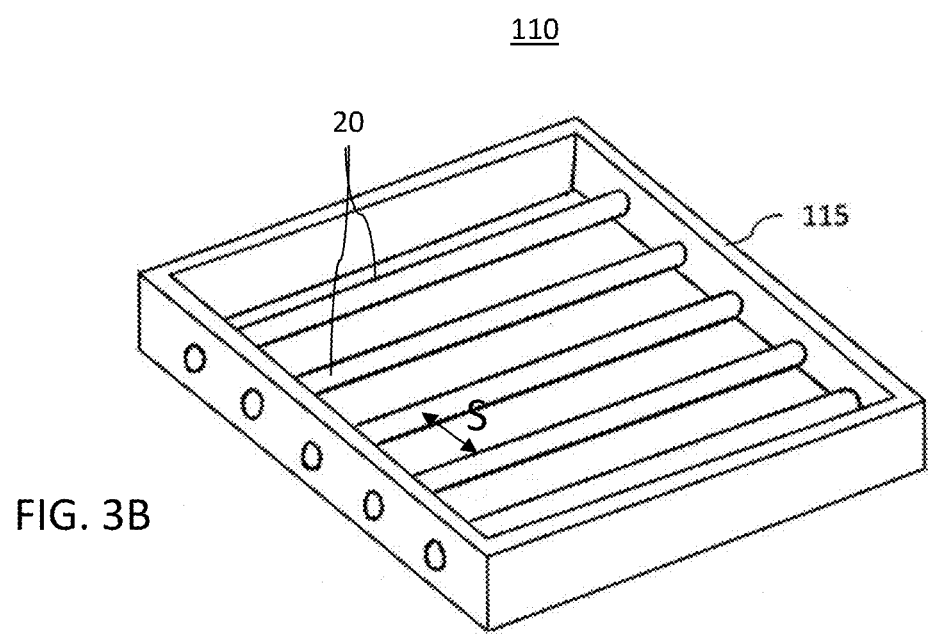
FIG. 3B is a schematic illustration of a plurality of radiation-attenuating rods in a parallel arrangement for providing anti-pinhole collimation in PET scan according to an embodiment of the present disclosure.

FIG. 3B shows a schematic illustration of an anti-pinhole collimation unit 110 comprising a plurality of radiation-attenuating rods 20 (herein after "absorber rods") that forms the anti-pinhole collimation unit according to an embodiment of the present disclosure. In this example, a set of the absorber rods 20 are arranged in a single layer in a parallel arrangement. In the illustrated example, a frame 115 holds the absorber rods 20 in the desired parallel arrangement. Other structural arrangements that can hold the absorber rods 20 in the desired arrangement are within the scope of this disclosure. The anti-pinhole collimation unit 110 is placed in the housing 100 in use for the practical purpose of being able to set the location for the anti-pinhole collimation unit 110 before the absorber rods are inserted into the housing 100.

Referring to FIG. 3C, a schematic illustration of a dual-orientation anti-pinhole collimation unit 120 according to some embodiments is disclosed. In the dual-orientation anti-pinhole collimation unit 120, there are two groups of absorber rods 20a and 20b that are crisscrossed orthogonal to each other thus being oriented in two different orientations. By placing this arrangement of absorber rods under a patient, for example, for performing a PET scan of the patient's prostate, the spatial resolution enhancement can be achieved in two directions at once. The plurality of absorber rods in the dual-orientation anti-pinhole collimation unit 120 can be held together in a housing similar to the housing 100 of FIG. 3A that is appropriately configured to hold the absorber rods 20a and 20b in the dual-orientation arrangement.

Figure 3E:
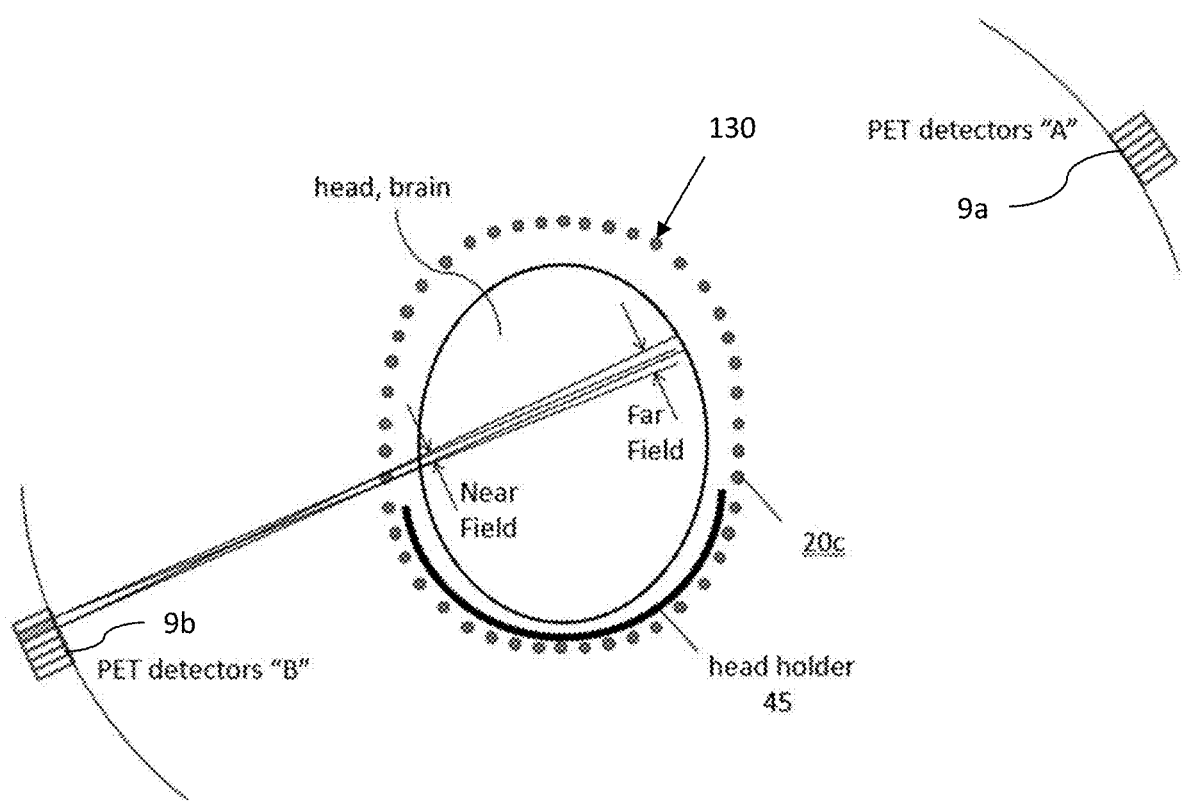
FIG. 3E is a schematic illustration of a plurality of radiation-attenuating rods in an arrangement for providing anti-pinhole collimation for brain PET scan according to some embodiments.

FIG. 3D is a schematic illustration of an anti-pinhole collimation unit 130 that is suitable for scanning a patient's brain according to another embodiment of the present disclosure. In the anti-pinhole collimation unit 130, a set of absorber rods 20c are arranged to surround the head of a patient and the absorber rods 20c are axially oriented with respect to the patient. In other words, the absorber rods 20c are oriented parallel to the head-to-toe direction with respect to the patient's anatomical direction. In the PET scan of the brain, the axially oriented absorber rods 20c provide spatial resolution enhancement in the direction orthogonal to the absorber rods 20c. In some embodiments, the absorber rods 20c can be held together in the arrangement shown by a plurality of connecting rods 20d as shown. The connecting rods 20d can be arranged in one or more ring-like arrangement holding the absorber rods 20c in the configuration. In some embodiments, if spatial resolution enhancement in the axial direction (i.e., along the head-to-toe direction) is also desired, the connecting rods 20d can be a second set of absorber rods. FIG. 3E is a schematic illustration of the anti-pinhole collimation unit 130 in the contemplated use condition. The patient's head is placed within the anti-pinhole collimation unit 130. A head holder 45 can be provided for holding the patient's head in position.

Figure 4:
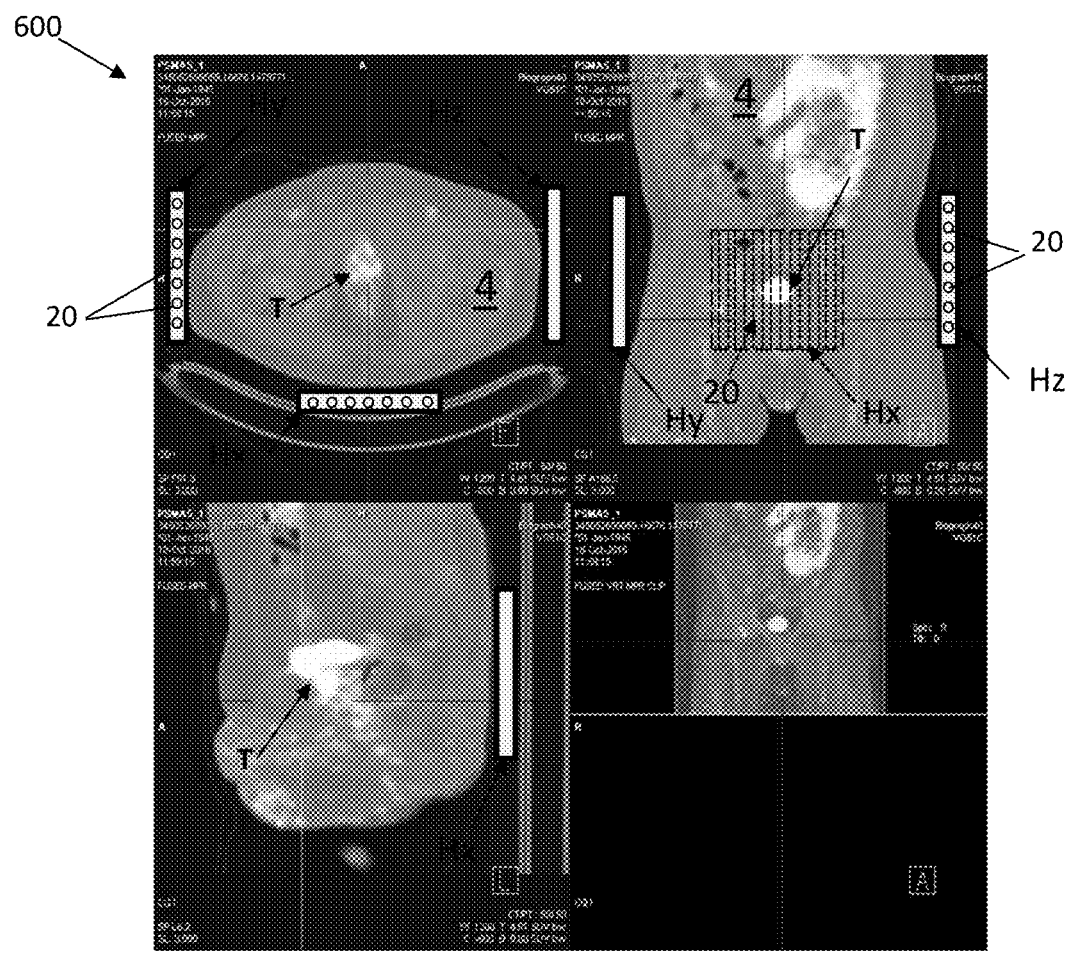
FIG. 4 is a composite PET scan views of a prostate region of a patient showing the positioning of the anti-pinhole rods according to the present disclosure.

Referring to FIG. 4, some examples of placements for the anti-pinhole collimation units 110 is shown overlaid on a composite 600 of PET scan views of a patient 4. In this example, the region of interest T for the PET scan is the prostate region of the patient and the array of the absorber rods 20 in the anti-pinhole collimation unit 110 are being used to improve the spatial resolution of the PET scan of the prostate region T. The various positions for the anti-pinhole collimation unit 110 is shown and labeled as Hx, Hy, and Hz with the letters x, y, and z denoting the anti-pinhole collimation direction (i.e., the improved spatial resolution being provided by the array of absorber rods 20) in terms of the patient's anatomical directions: left-to-right direction (represented by "x"), front-to-back direction (represented by "y"), and head-to-toe direction (represented by "z"). Thus, the letters x, y, and z also denotes the orientation of the absorber rods 20 in the anti-pinhole collimation units. For example, the anti-pinhole collimation position Hx denotes that the plurality of the absorber rods 20 in the anti-pinhole collimation unit 110 placed there are collimating (improving the spatial resolution of the PET scan) in direction x (the left-to-right direction) and, thus, the absorber rods themselves are oriented orthogonal to the patient's left-to-right direction, the collimation direction. Accordingly, in the upper left corner of the composite image 600 showing the transverse view of the patient 4, the anti-pinhole collimation unit 110 in anti-pinhole collimation position Hx is shown with a row of circles representing the cross-sectional views of the absorber rods 20 that are oriented orthogonal to the patient's left-to-right direction (i.e., the absorber rods are oriented parallel to the patient's head-to-toe direction). In the upper right corner of the composite image 600 showing the frontal plane view from the front side of the patient, the anti-pinhole collimation position Hx under the patient is shown with dashed lines. The corresponding orientation of the absorber rods 20 are also shown with a set of parallel dashed lines. In the lower left corner of the composite image 600 showing the median plane (a plane cutting through the patient in the front-to-back direction and extending head-to-toe) view of the patient, the anti-pinhole collimation position Hx is under the patient.

The anti-pinhole collimation position Hy denotes that the plurality of the absorber bars 20 placed there are collimating (improving the spatial resolution of the PET scan) in direction y (the front-to-back direction) and, thus, the absorber rods are oriented orthogonal to the patient's front-to-back direction, the collimation direction. Accordingly, in the upper left corner of the composite image 600, the anti-pinhole collimation unit 110 in anti-pinhole collimation position Hy is shown with a row of circles representing the cross-sectional views of the absorber rods 20 that are oriented parallel to the patient's head-to-toe direction (or orthogonal to the front-to-back direction). In the upper right corner of the composite image 600, the aborber rods in the anti-pinhole collimation position Hy are in parallel orientation to the head-to-toe direction.

The anti-pinhole collimation position Hz denotes that the plurality of the absorber rods 20 placed there are collimating (improving the spatial resolution of the PET scan) in direction z (the head-to-toe direction) and, thus, the absorber rods 20 are oriented in the direction orthogonal to the patient's head-to-toe direction. Accordingly, in the upper left corner of the composite imabe 600, the absorber rods 20 in the anti-pinhole collimation position Hz are in parallel orientation to the front-to-back direction. In the upper right corner of the composite image 600, the anti-pinhole collimation unit 110 in the anti-pinhole collimation position Hz are shown with a row of circles representing the cross-sectional views of the absorber rods 20 oriented orthogonal to the patient's head-to-toe direction.

A PET scan can be conducted with anti-pinhole collimation units, comprising a plurality of absorber rods, in place in one, two, or all three of the possible anti-pinhole collimation positions Hx, Hy, and Hz, thus generating a projection data. Whether one, two, or all three orientations are utilized at once will depend on which direction the spatial resolution improvement is desired. Then, a PET image is reconstructed from the resulting projection data.

In some embodiments, a PET scan can be conducted with anti-pinhole collimation units, comprising a plurality of absorber rods, in one of the possible anti-pinhole collimation positions Hx, Hy, and Hz, generating a projection data, re-orient the anti-pinhole collimation unit to a different orientation, then conduct a second PET scan generating a second projection data. Then, a PET image is reconstructed from the two projection data.

In another embodiment, the anti-pinhole collimation unit can be re-oriented to a third orientation after the second PET scan, then conduct a third PET scan generating a third projection data. Then, a PET image is reconstructed from the three projection data. The third orientation is different from the first orientation and the second orientation.

In some embodiments, a PET scan is conducted without the plurality of absorber rods in place to generate a first projection data that is a non-collimated data that does not include the enhanced spatial resolution. Then, place a plurality of absorber rods in one, two, or all three of the anti-pinhole collimation positions Hx, Hy, and Hz, and conduct a PET scan generating a second projection data that is a collimated data. Then, reconstruct a PET image from the two projection data by combining the two data within an image reconstruction algorithm.

Figure 5:
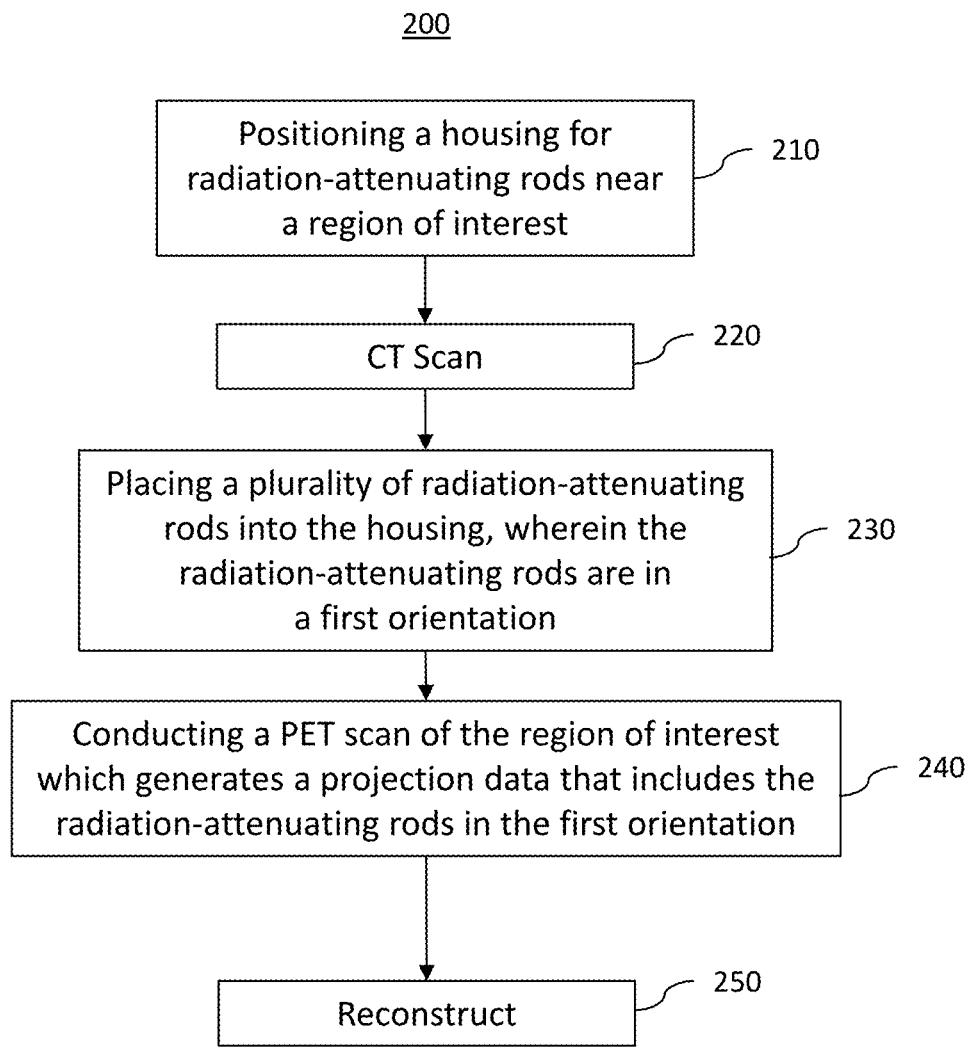
FIG. 5 is a flowchart of a method according to an embodiment of the present disclosure.

Referring to the flowchart 200 in FIG. 5, a method for imaging a region of interest (a target region) in a patient using a PET scanner according to some embodiments is disclosed. The method comprises positioning a housing 100 for absorber rods at a location that is within the field of view of the PET scanner when scanning the region of interest T. See block 210. The housing 100 is positioned closer to the region of interest T than the detectors associated with the PET scanner. The housing 100 is configured for holding a plurality of absorber rods 20 in a parallel arrangement such that when the plurality of absorber rods are placed in the housing, all of the plurality of absorber rods 20 are in a first anti-pinhole collimation orientation with respect to the patient.

After the step of block 210, the method further comprises conducting a CT scan to obtain diagnostic information on the region of interest, and more importantly, for determining the location of the housing 100, and thus the location of each absorber rods 20 that would be placed in the housing, in the PET scanner's field of view. This CT scan is a calibration step to determine the location of each absorber rods. See block 220. Next, the method further comprises placing the plurality of absorber rods 20 into the housing 100, wherein the plurality of absorber rods are in the first anti-pinhole collimation orientation. See block 230. Next, the method further comprises conducting a PET scan of the region of interest generating a projection data that includes the spatial resolution enhancement effects of the absorber rods. See block 240. Next, an image of the region of interest is reconstructed from the projection data. See block 250.

In some embodiments of the method, the first anti-pinhole collimation orientation is parallel to the collimation direction z (the patient's head-to-toe direction), collimation direction y (the front-to-back direction), or collimation direction x (the left-to-right direction). In other words, the housing 100 can be positioned such that in the first anti-pinhole collimation orientation, the plurality of the absorber rods 20 placed in the housing 100 are parallel to one of the three anatomical directions of the patient: (1) the head-to-toe direction; (2) the front-to-back direction; and (3) the left-to-right direction.

In some embodiments of the method illustrated in the flowchart 200, the method can further comprise a step of first identifying the region of interest T by X-ray topogram or camera scan before the step of positioning the housing 100 in block 210.

Figure 6:
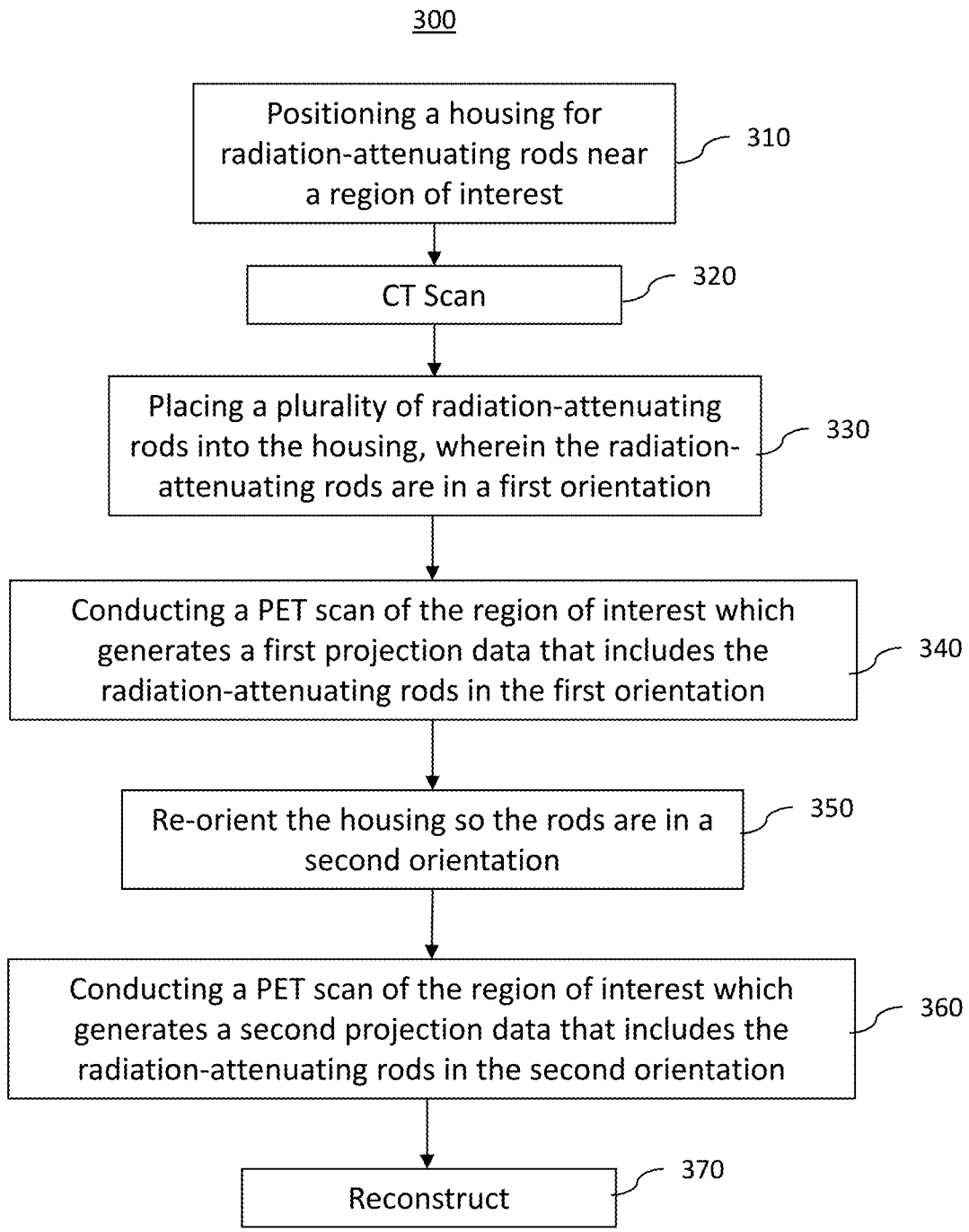
FIG. 6 is a flowchart of a method according to another embodiment of the present disclosure.

Referring to FIG. 6, according to another aspect of the present disclosure, another method or a process flow 300 for generating a PET scan image with improved spatial resolution is disclosed. In this embodiment, imaging a region of interest in a patient using a PET scanner comprises positioning a housing 100 for absorber rods at a location that is within the field of view of the PET scanner when scanning the region of interest T, wherein the housing is positioned closer to the region of interest T than the detectors associated with the PET scanner, wherein the housing 100 is configured for holding a plurality of absorber rods in a parallel arrangement such that when a plurality of absorber rods 20 are placed in the housing, all of the plurality of absorber rods are in a first anti-pinhole collimation orientation with respect to the patient. See block 310.

Next, the method further comprises conducting a CT scan to obtain diagnostic information on the region of interest and for determining the location of the housing 100, and thus the location of each absorber rods 20 that would be placed in the housing, in the PET scanner's field of view. This CT scan is a calibration step to determine the location of each absorber rods. See block 320. Next, the method further comprises placing a plurality of absorber rods 20 into the housing 100, wherein the plurality of absorber rods are in the first anti-pinhole collimation orientation. See block 330. Next, the method further comprises conducting a PET scan of the region of interest generating a first projection data that includes the spatial resolution enhancement effects of the absorber rods 20 in the first anti-pinhole collimation orientation. See block 340. Next, the housing 100 is re-oriented to a new position so that the plurality of absorber rods 20 are in a second anti-pinhole collimation orientation with respect to the patient. See block 350. Next, the method further comprises conducting a PET scan of the region of interest generating a second projection data that includes the spatial resolution enhancement effects of the absorber rods 20 in the second anti-pinhole collimation orientation. See block 360. Next, a PET image of the region of interest is T reconstructed from the first and second projection data. See block 370.

In some embodiments of the method illustrated in the flowchart 300, the first anti-pinhole collimation orientation and the second anti-pinhole collimation orientation are different and each one is one of the three anti-pinhole collimation directions x, y, and z described herein.

In some embodiments, the method illustrated in the flowchart 300 further comprises a step of identifying the region of interest T, thus the location of the region of interest T in the field of view of the PET scanner, by X-ray topogram before the step of positioning the housing 100. This allows accurate positioning of the housing 100 near the region of interest T. In some embodiments, instead of X-ray topogram, an optical technique can be used to identify and locate the region of interest T. For example, digital cameras or 3D cameras can be used to perform an optical scan of the patient and identify the region of interest T.

Figure 7:
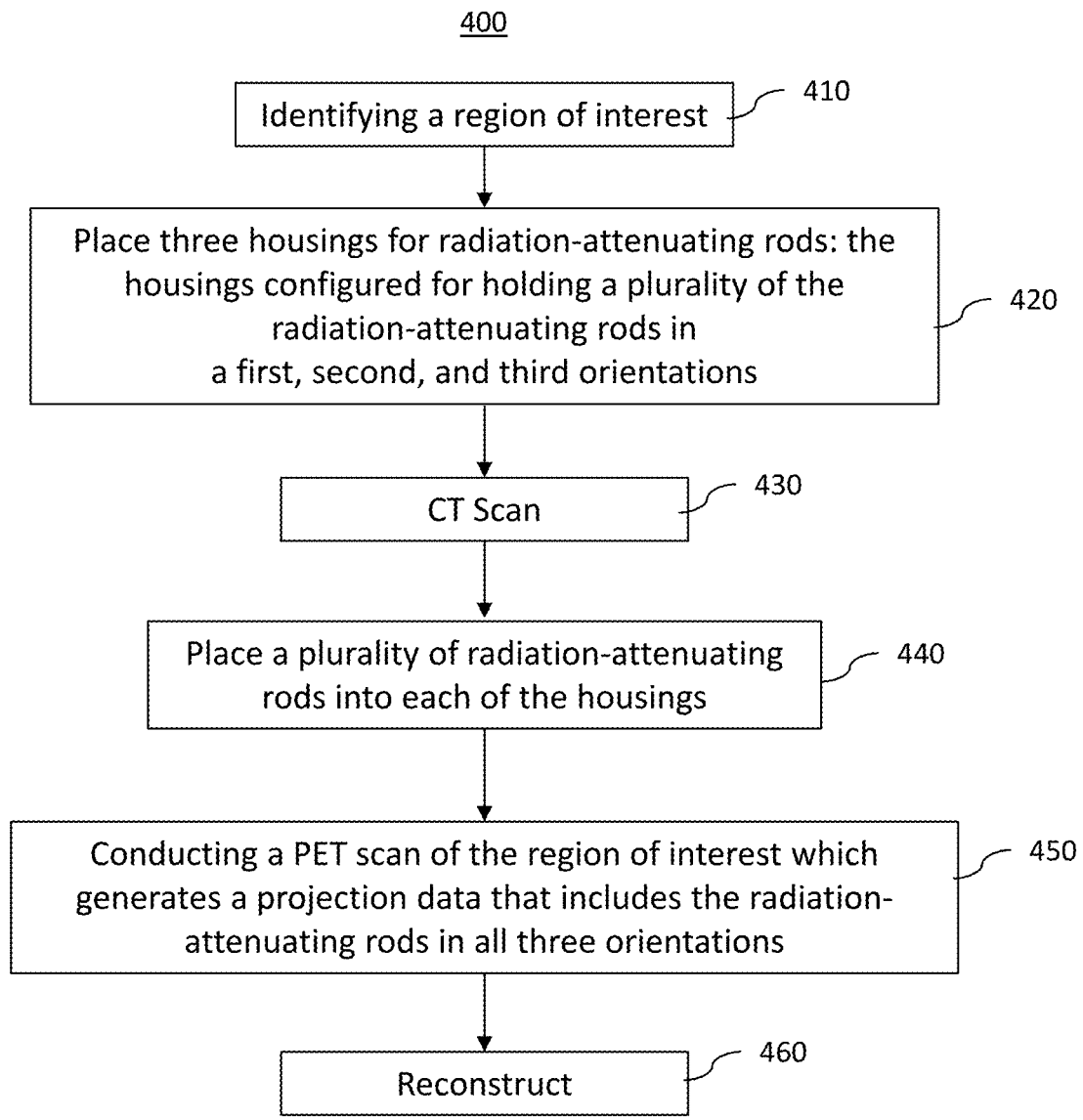
FIG. 7 is a flowchart of a method according to another embodiment of the present disclosure.

Referring to FIG. 7, according to another aspect of the present disclosure, another method or a process flow 400 for generating a PET scan image with improved spatial resolution is disclosed. In this embodiment, imaging a patient using a PET scanner comprises positioning three housings 100 for absorber rods in three different locations that are within the field of view of the PET scanner when scanning the region of interest T. Each of the housing is positioned closer to the region of interest T than the detectors associated with the PET scanner. Each housing is configured to hold a plurality of absorber rods 20 in a parallel arrangement to form an anti-pinhole collimation unit. The three housings are placed such that when the plurality of absorber rods are placed in each of the three housings, the resulting anti-pinhole collimation units are in a first, second, and third collimation orientations with respect to the region of interest. See block 420. The first, second, and third collimation orientations are parallel to the collimation directions x, y, and z.

Next, the method further comprises conducting a CT scan to obtain diagnostic information on the region of interest and for determining the locations of the housings, and thus the location of each absorber rods 20 that would be placed in the housings, in the PET scanner's field of view. This CT scan is a calibration step to determine the location of each absorber rods. See block 430. Next, the method of flowchart 400 further comprises placing a plurality of absorber rods 20 into each of the three housings, wherein the plurality of absorber rods in each of the three housings are in the first, second, and third orientations that are parallel to the collimation directions x, y, and z. See block 440. Next, the method further comprises conducting a PET scan of the region of interest generating a projection data that includes the anti-pinhole collimation (the spatial resolution enhancement effects of the absorber rods 20) in all three directions. See block 450. Next, the method further comprises reconstructing a PET image of the region of interest T from the projection data. See block 460.

In some embodiments, the method illustrated in the flowchart 400 further comprises a step of identifying the region of interest T by X-ray topogram or an optical scan before the step of positioning the housing. See block 410.

Figure 8:
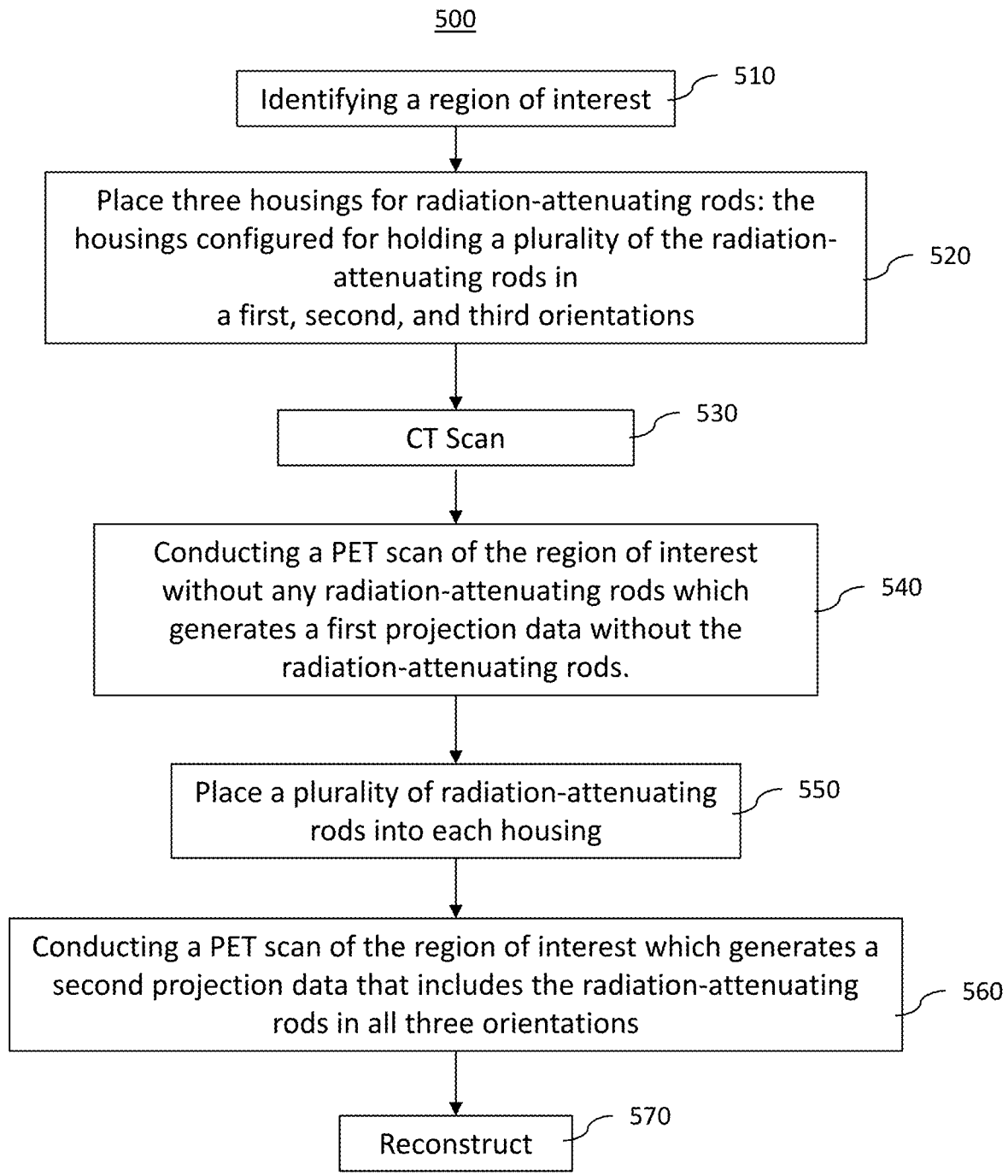
FIG. 8 is a flowchart of a method according to another embodiment of the present disclosure.

Referring to FIG. 8, according to another aspect of the present disclosure, another method or a process flow 500 for generating a PET scan image with improved spatial resolution is disclosed. In this embodiment, the method comprises positioning three housings 100 near the region of interest T, wherein each housing is within the field of view of the PET scanner when scanning the region of interest T. Each housing is closer to the region of interest T than the detectors associated with the PET scanner. Each housing is configured to hold a plurality of absorber rods 20 in a parallel arrangement and the three housings are placed such that when the plurality of absorber rods are placed in each of the three housings, the absorber rods in the first housing are in a first orientation, the absorber rods in the second housing are in a second orientation, and the absorber rods in the third housing are in a third orientation, with respect to the region of interest. See block 520.

Next, the method further comprises conducting a CT scan to obtain diagnostic information on the region of interest T and for determining the locations of the housings 100, and thus the location of each absorber rods 20 that would be placed in the housings, in the PET scanner's field of view. This CT scan is a calibration step to determine the location of each absorber rods. See block 530. Next, the method further comprises conducting a PET scan of the region of interest T generating a first projection data that does not include the spatial resolution enhancement effects of the absorber rods. See block 540. Next, the method further comprises placing a plurality of absorber rods 20 into each of the three housings, wherein the plurality of absorber rods in each of the three housings are in the first, second, and third orientations. See block 550. Next, the method further comprises conducting a PET scan of the region of interest generating a second projection data that includes the spatial resolution enhancement effects of the absorber rods in the first, second, and third orientations. See block 560. The first, second, and third orientations can be parallel to the collimation directions x, y, and z. Next, the method further comprises constructing a PET image of the region of interest T from the two projection data. See block 570.

In some embodiments, the method illustrated in the flowchart 500 further comprises a step of identifying the region of interest T by X-ray topogram or an optical scan before the step of positioning the housing. See block 510.

The method of the present disclosure, including the various embodiments, represented by one or more blocks of the respective flowcharts, and combinations of blocks in the flowcharts, can be implemented by computer program instructions. These computer program instructions can be stored in memory and provided to a processor of a general purpose computer, special purpose computer, and/or other programmable data processing apparatus such that the computer program instructions, when executed via the processor of the computer and/or other programmable data processing apparatus, implement the steps/acts specified in the flowchart blocks and/or the associated description. In other words, the steps/acts can be implemented by a system comprising a processor that can access the computer-executable instructions that are stored in a non-transitory memory. In the context of the present disclosure, the data processing and control unit 6 can be the processor that executes such computer program instructions. The data processing and control unit 6 can comprise a non-transitory, machine readable storage medium 10 that can store the computer program instructions. In other embodiments, the computer program instructions can also be stored in an externally provided storage medium 12 discussed in conjunction with FIG. 1A.

Figure 9:
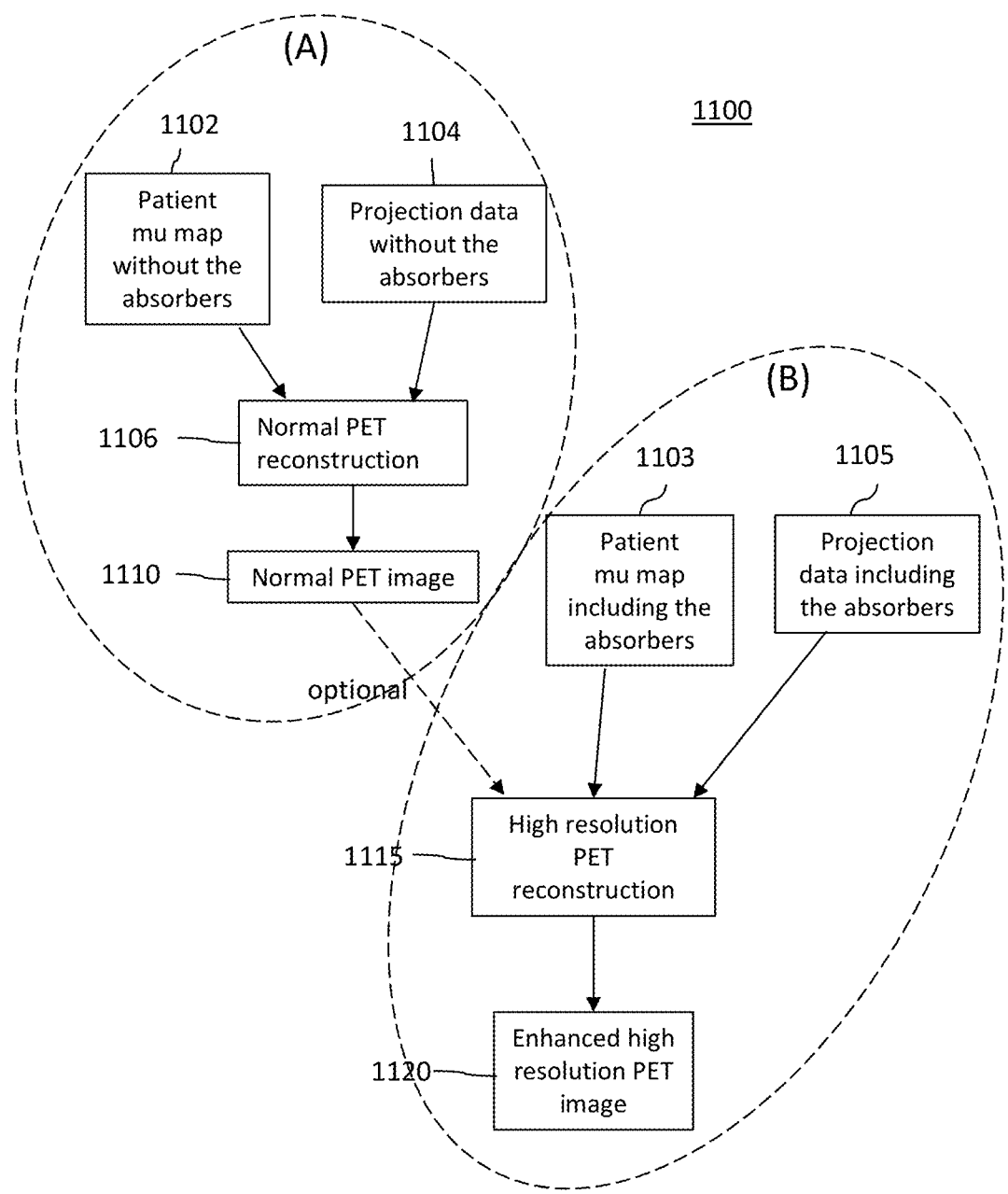
FIG. 9 is a flowchart of the image reconstruction process according to an embodiment of the present disclosure.

FIG. 9 shows a high level flowchart of the image reconstruction process according to the present disclosure. The left side (A) of the flowchart depicts a normal PET scan reconstruction process. Here, "normal" refers to non-collimated, i.e., PET scan without the anti-pinhole collimating absorber rods in place. In normal PET reconstruction 1106, the reconstruction algorithm incorporates patient μ map without the absorbers 1102 and PET scan projection data generated without the absorbers 1104 are processed through the reconstruction algorithm and generates normal PET image 1110. μ map refers to a map containing information on how various regions of the patient body attenuates gamma ray. In the case of the collimated PET scan, the μ map incorporates the additional gamma ray attenuation resulting from the anti-pinhole absorber rods. The right side (B) of the flowchart depicts a collimated PET scan reconstruction process. Patient μ map including the absorbers 1103 and PET scan projection data generated with the absorbers 1105 are processed through the reconstruction algorithm 1115 and generates enhanced high resolution PET image 1120.

In some embodiments, the collimated PET scan reconstruction process can optionally combine the normal PET image 1110 obtained from a normal PET scan. The normal PET scan has a low level of distortion due to image noise. Image reconstruction methods can be improved (reducing image noise) by mathematically and computationally imposing a constraint that a region reconstructed with higher resolution must contain the same total activity as the same region reconstructed with lower or normal resolution.

The absorber rods 20 are elongated structures whose cross-section can have any shape such as a triangle, square, pentagon, hexagon, etc. Preferably, the absorber rods are cylindrical structures because they present uniform profile to the PET scanner detectors from all angles. Cylindrical absorber rods would provide the optimal linear collimation effect for enhancing the spatial resolution of the PET scan. The absorber rods 20 can be made from materials that can absorb gamma photon radiation. Some examples of suitable materials for the absorber rods are tungsten, tantalum, thorium, lead, gold, stainless steel, and uranium. In some embodiments, the absorber rods are preferably made of tungsten. The 511-keV photon attenuation length of tungsten, tantalum, thorium, lead, gold, stainless steel, and uranium are: 3.9 mm (tungsten), 4.6 mm (tantalum), 4.9 mm (thorium), 5.6 mm (lead), 3.5 mm (gold), 15.3 mm (steel), and 2.8 mm (uranium). The diameter of the absorber rods 20 is preferably less than two times the 511-keV photon attenuation length of the material. For practical consideration, the diameter of the absorber rods would be at least 0.5 mm because that is well less than the size of a PET detector crystal. Attenuation length, also referred to as absorption length, is the distance into a material when the probability has dropped to 1/e that a particle has not been absorbed. Alternatively, for a beam of particles incident on the material, the attenuation length is the distance where the intensity of the beam has dropped to 1/e, or about 63% of the particles have been stopped.

In some embodiments, the plurality of absorber rods 20 are spaced one diameter apart in the housing 100. The use of a large number of absorbers increases the sensitivity by absorbing more radiation. Although a very close spacing is desirable in the system design for that reason, one selects a spacing of about one diameter so that radiation is never blocked by more than one absorber. In other words, considering the various angles for LORs that would be encountered in a PET scanner ring, it is desirable that two adjacent absorber rods do not intercept a LOR and only one absorber bar blocks the gamma photon radiation.

Experimental

Figure 10:
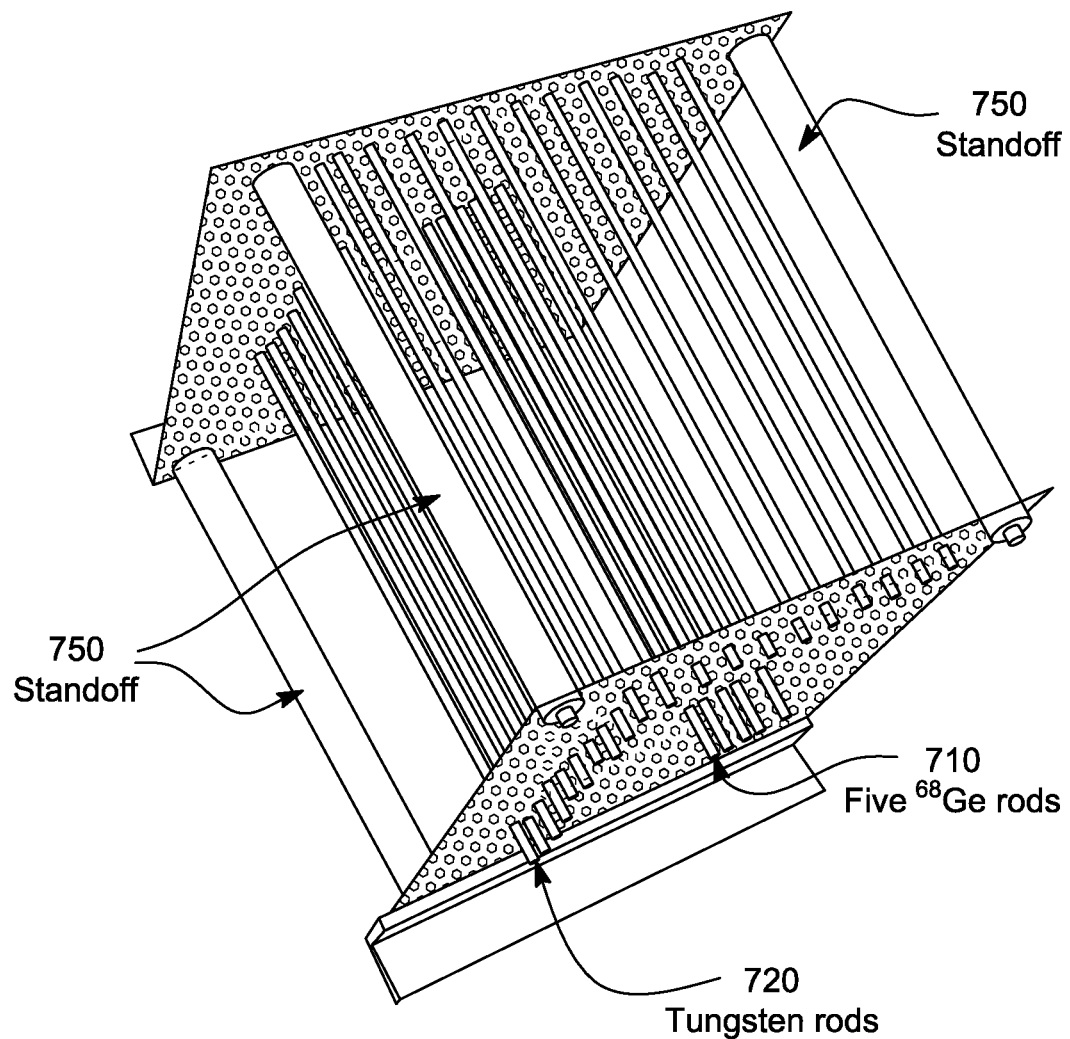
FIG. 10 is a photograph showing the first experimental setup used to verify the anti-pinhole collimation effect according to the present disclosure.

FIG. 10 is a photograph showing the first experimental setup used to verify the anti-pinhole collimation effect of a plurality of anti-pinhole collimators (a plurality of radiation-attenuating rods) 720 in parallel arrangement according to an embodiment of the present disclosure. The setup comprised of five $^{68}$Ge rods 710 as the phantom gamma radiation source and twenty absorber rods 720 made of tungsten in parallel arrangement as the anti-pinhole collimators. The $^{68}$Ge rods 710 were standard rod source with an inner core of $^{68}$Ge-laden epoxy surrounded by a stainless steel tube with inner diameter of 1.68 mm and outer diameter of 2.29 mm. The radioactivity was distributed in a nominal length of 16.73 cm. The rods stopped many of the emitted positrons, providing a PET signal, but could not stop all of them since the wall thickness was only 0.30 mm. The $^{68}$Ge rod source activities were nominally 1 mCi (37 MBq)±10% on the days the experiments were carried out.

Twenty absorber rods 720 were used as the radiation attenuating anti-pinhole collimators. These were ground tungsten electrodes, ⅛ inch diameter (3.18 mm), nominally 7 inches long but actually about 17.4 cm (6.85 inch).

A grid of regularly spaced x-y positions for the $^{68}$Ge rods 710 and the absorber rods 720 were established using two approximately parallel perforated brass screens in which holes with diameter 0.138 inch (3.505 mm) were separated horizontally and vertically by 0.188 inch (4.775 mm). The screens were oriented transaxially and were about 150 mm apart.

Figure 11A:
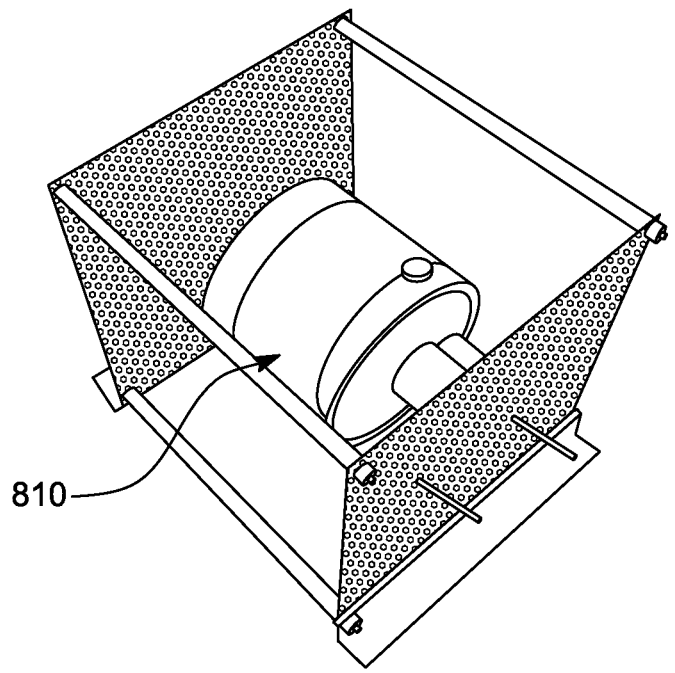
FIGS. 11A and 11B are photographs showing the second experimental setup used to verify the anti-pinhole collimation effect according to the present disclosure.
Figure 11B:
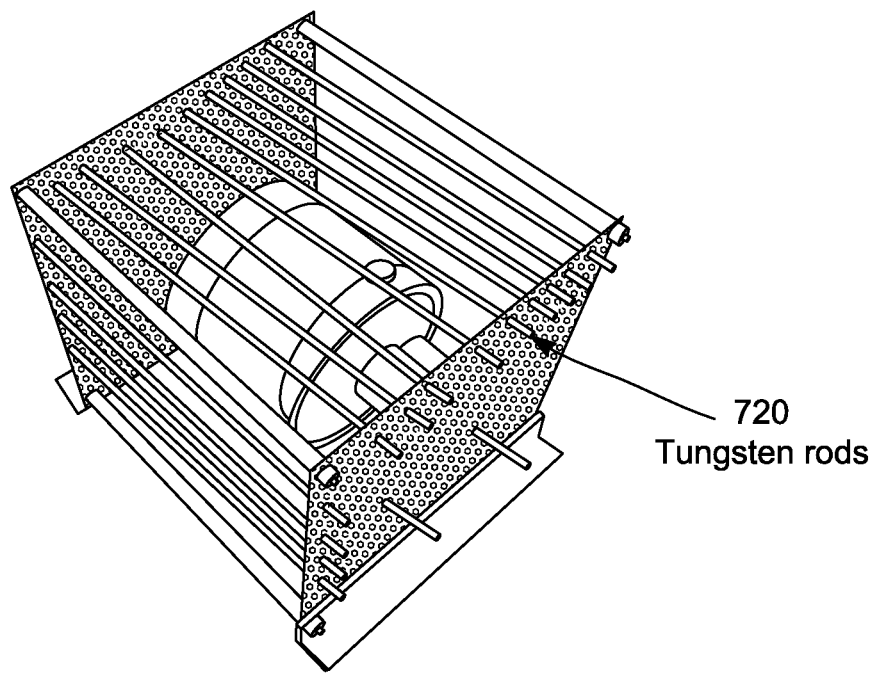

FIGS. 11A and 11B are photographs showing the second experimental setup in which a mini-Derenzo phantom 810 with $^{18}$F radioactivity in solution was used as the radiation source. The mini-Derenzo phantom 810 was loaded with about 25 ml of water in which $^{18}$F radioactivity was dissolved. The amount of activity in the phantom was about 1 mCi.

FIG. 12 shows the grid of x-y positions for the five $^{68}$Ge rods 710 and twenty absorber rods 720 used in the experiment. The grid consisted of ten positions horizontally ordered H1 to H10, spaced 2×4.775 mm=9.55 mm apart, and ten vertically ordered positions V1 to V10, also 9.55 mm apart. There were five horizontally ordered positions, C1 to C5, with a spacing of 4.775 mm between positions C1 and C2, and between C3 and C4. The spacing between C2 and C3, and C4 and C5 were 9.55 mm. The position C1 was directly below H4. The position C5 was directly below H7. Vertically, the positions C1 through C5 were halfway between V5 and V6. The setup was positioned in the scanner so that the center of the CT field of view was near C2.

The experiment included nine PET/CT scans with various arrangements of radiation emitters and the tungsten rods:

| | |
|---|---|
| Scan 1 | A $^{68}$Ge rod was in position that is one hole lower (4.775 mm) than C2; No absorber rods. |
| Scan 2 | A $^{68}$Ge rod was in position H1; No absorber rods. |
| Scan 4 | A $^{68}$Ge rod was in position V1; No absorber rods. |
| Scan 5 | A $^{68}$Ge rod was in position V10; No absorber rods. |
| Scan 6 | Five $^{68}$Ge rods were in positions C1, C2, C3, C4 and C5; No absorber rods. |
| Scan 7 | Five $^{68}$Ge rods were in positions C1, C2, C3, C4 and C5; Absorber rods in positions H1 to H10 and V1 to V10. |
| Scan 8 | The mini-Derenzo phantom was positioned near the middle and absorber rods in positions H1 to H10 and V1 to V10. The mini-Derenzo phantom was suspended on wooden dowel rods. |
| Scan 9 | Same as scan 8, without the absorber rods. |

PET/CT scans 1-5 determined the positions of $^{68}$Ge rods in positions C2, H1, H10, V1, V10. Centroid of the $^{68}$Ge rod at each position were extracted in both CT and PET images. Results are shown in Table 1.

TABLE 1

| | Source x and y coordinates (mm) | | | |
|---|---|---|---|---|
| | x (PET) | y (PET) | x (CT) | y (CT) |
| C2* | 1.42 | −162.14 | 0.95 | −161.52 |
| H1 | −31.91 | −214.19 | −32.25 | −213.48 |
| H10 | 54.54 | −214.18 | 54.26 | −213.70 |
| V1 | −36.28 | −209.43 | −36.62 | −208.81 |
| V10 | −36.76 | −123.64 | −36.92 | −122.98 |

*The actual C2 position in the setup was 4.775 mm higher than the y coordinate position shown here in Table 1 since the $^{68}$Ge rod was placed one hole lower than C2 position.

CT and PET centroids agreed within 0.7 mm. The absorber rods 720 were expected to sit at the same x coordinates but at slightly higher positions (more negative y coordinates) because the radius of the absorber rods was 0.445 mm greater than the $^{68}$Ge rods. In our interpretation of scans 7 and 8, the rod positions H2 to H9 and V2 to V9 were estimated by interpolation.

Figures 13A, 13B:
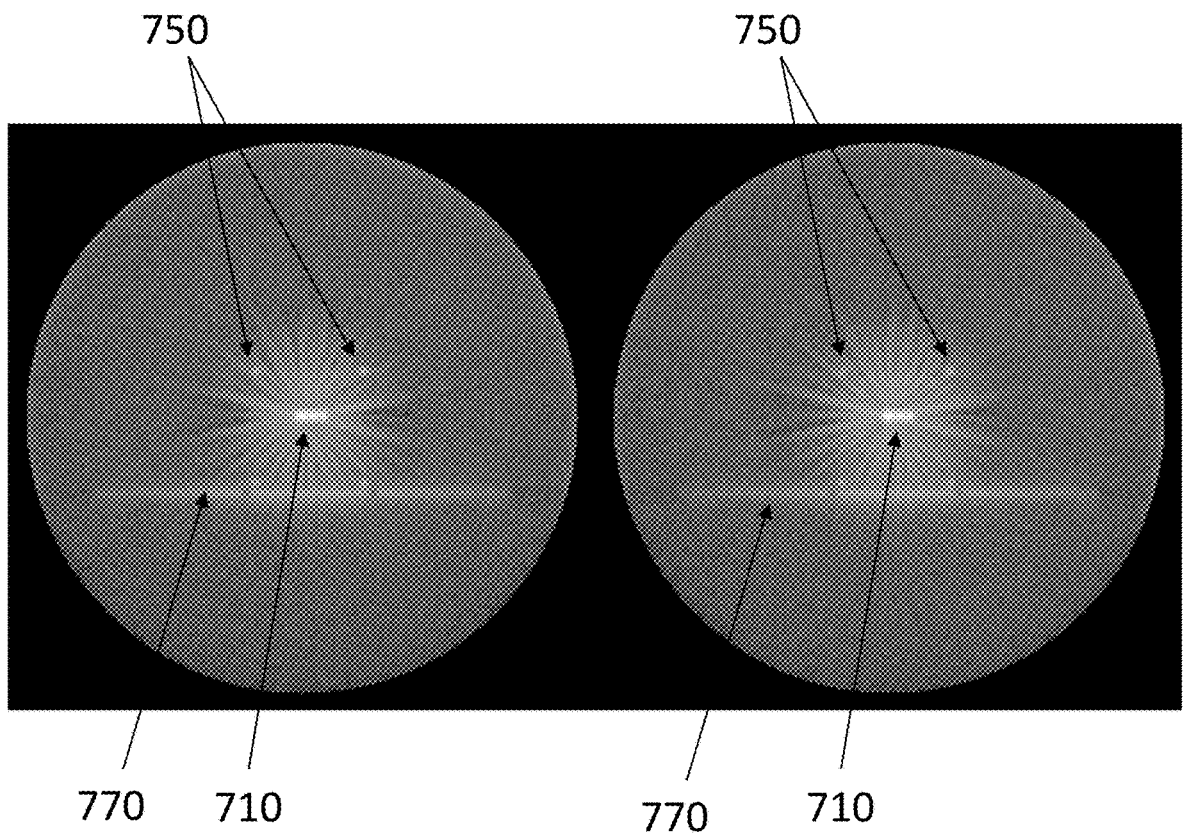
FIG. 13A is a PET image of an experimental setup according to the present disclosure.
FIG. 13B is a PET image of an experimental setup according to the present disclosure.

The PET images from scans 6 and 7 are presented in FIGS. 13A and 13B, respectively. Non-attenuation corrected (NAC) iteratively reconstructed images were used. All slices were summed. The PET images in FIGS. 13A and 13B show positrons that struck the table (the horizontal line) 770 on which the experimental setup was placed and the standoffs 750. The $^{68}$Ge rods 710 at positions C1 to C5 are shown.

Figure 14:
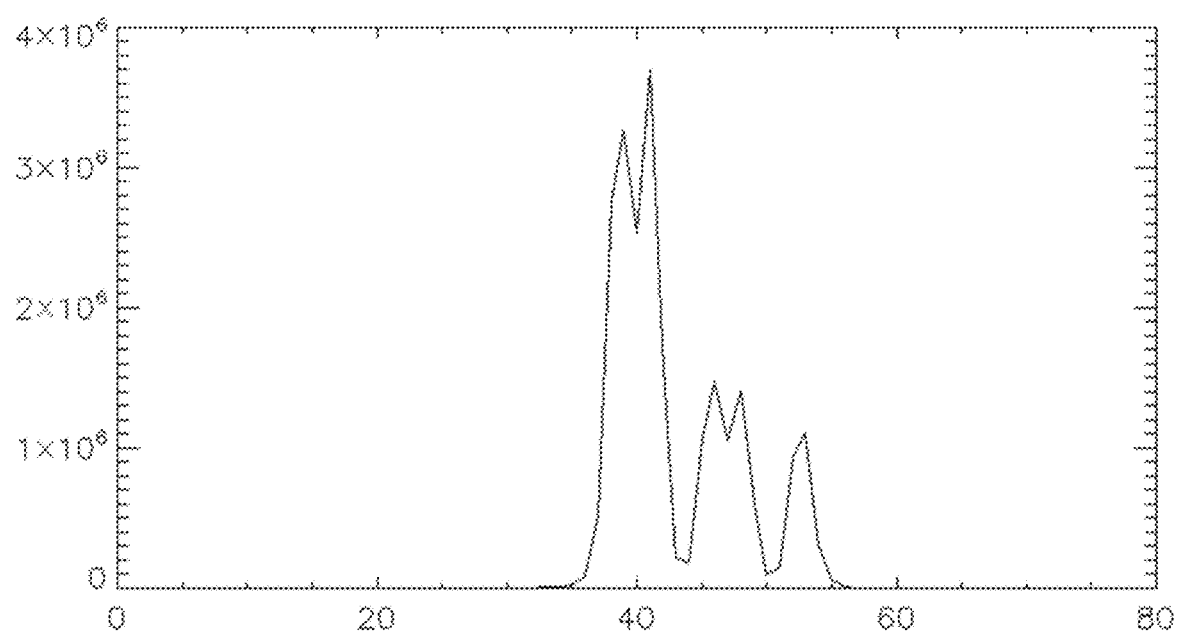
FIG. 14 is a plot Position resolution based on normal PET reconstruction.

FIG. 14 illustrates the spatial resolution in normal PET/CT by showing the central image slice and a profile through the $^{68}$Ge rods 710 in positions C1 to C5. The $^{68}$Ge rods separated by 4.775 mm (the spacing between positions C1 and C2, and between positions C3 and C4) were barely resolved, with a peak to valley ratio of about 1.25. The rods separated by 9.55 mm (the spacing between positions C2 and C3, and between positions C4 and C5) were well resolved.

Anti-pinhole PET scan concept of the present disclosure was tested with the following approach. Sinograms from scans 6, 7, 8 and 9 were summed over all planes. We formed a difference sinogram for each phantom, using the following equation:

$$\text{difference sinogram} = \text{sinogram1} - \text{sinogram2} \times (\text{decay correction}), \quad \text{(EQ 1)}$$

where sinogram2 was generated with the absorber rods in place and sinogram1 did not. The decay correction was used in the comparison of scans 8 and 9, and was set to a value of 1 in the comparison of scans 6 and 7.

Figure 15A:
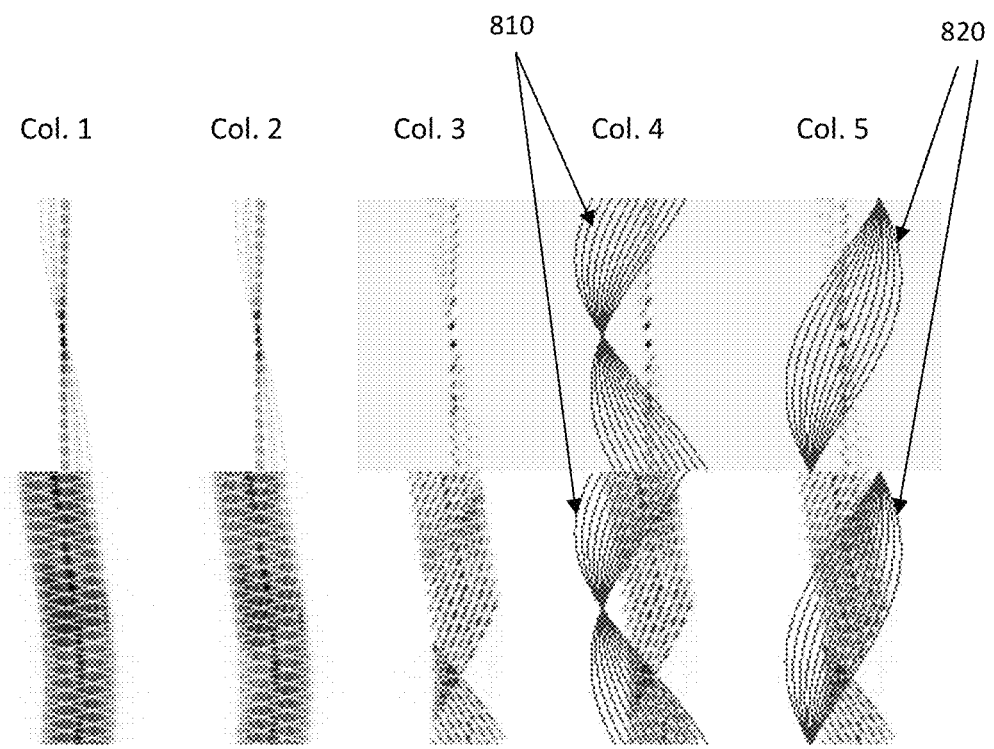
FIGS. 15A and 15B shows sinograms generated from an experimental PET scan conducted with anti-pinhole collimation set up according to the present disclosure.

FIG. 15A shows the sinograms including the difference sinogram defined by EQ 1. The location of each absorber rods was known from a calibration CT scan. The figure shows the regions of sinogram space occupied by each of the twenty absorber rods used in the experiment. Each absorber rod corresponded to the space between two solid lines. The top row is the sinogram based on the phantom of five $^{68}$Ge rods from scans 6 and 7. The bottom row is the sinogram based on the mini-Derenzo phantom from scans 8 and 9. There are five columns in FIG. 15A. Column 1 on the left is sinogram1. Column 2 is sinogram2. Columns 3, 4, 5 are the difference sinograms. Each of the space between two adjacent solid lines 810 in column 4 show regions occupied by the absorber rods at positions H1 to H10. Each of the space between two adjacent solid lines 820 in column 5 show regions occupied by the absorber rods at positions V1 to V10, based on the values provided in Table 1. Having demarked the sinogram into regions between the solid lines 810, 820, we can transform the PET measurement, which is based on two coincident gamma rays, into a set of single-photon measurements, one for each absorber rod (an anti-pinhole); and each single-photon measurement is not blurred by non-collinearity. This transformation was made by summing the difference sinogram in the radial direction (sinogram radial binds correspond to the horizontal direction in the illustration), but only from one solid line to the next. This results in a measurement of all the flux that was absorbed by each cylinder, as a function of angle (sinogram angle bins correspond to the vertical direction in the illustration). This is closely analogous to what happens when radiation passes through an actual pinhole.

Figure 15B:
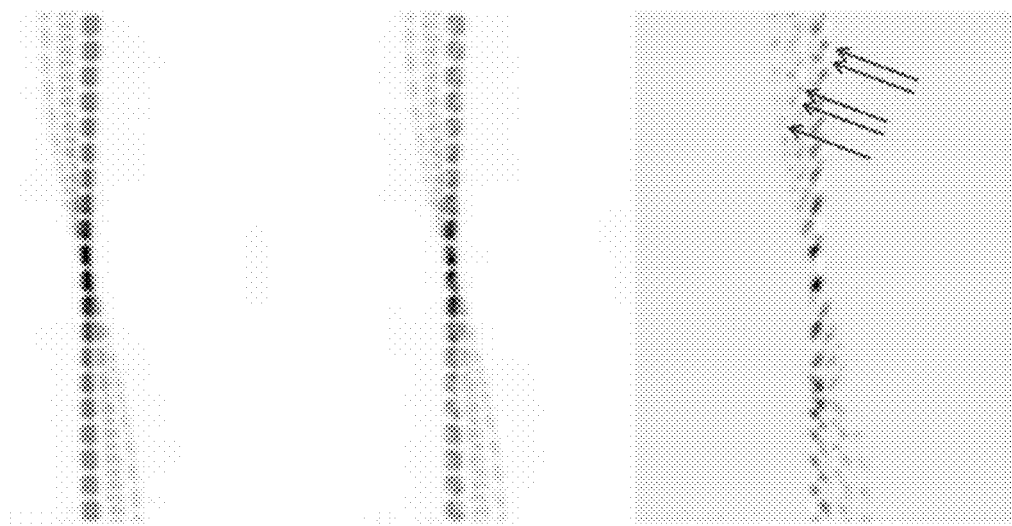

FIG. 15B shows the upper left portion of columns 1, 2, and 3 from the sinograms in FIG. 15A and the arrows point out the five $^{68}$Ge rods in positions C1 through C5 that are better resolved in the difference sinogram, thus, illustrating enhanced spatial resolution. This shows that anti-pinhole collimation PET scan using the radiation-attenuating tungsten rods in parallel arrangement exhibited improved spatial resolution of the $^{68}$Ge rods positions.

Figure 15C:
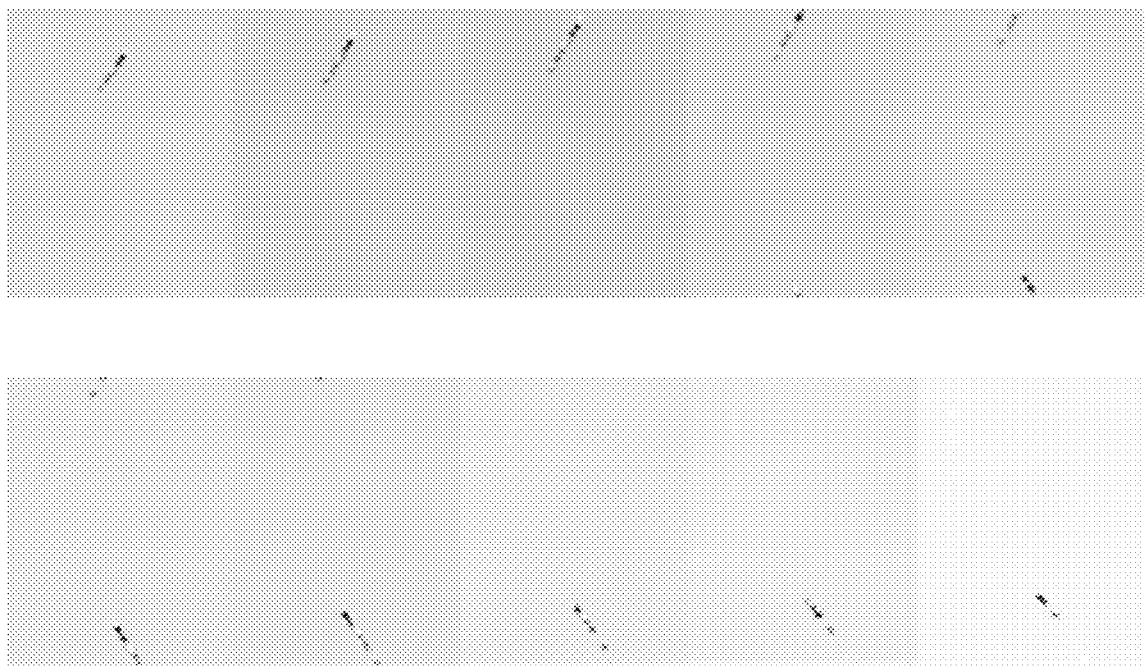
FIG. 15C shows sinogram fragments corresponding to the radiation-attenuating tungsten rods in positions H1 to H5 (top row) and H6 to H10 (bottom row).

FIG. 15C shows sinogram fragments that were outlined by the solid curves 810 and 820 in FIG. 15A. The sinogram fragments correspond to the radiation-attenuating tungsten rods 720 in positions H1 to H5 (top row) and H6 to H10 (bottom row). In this representation, the individual $^{68}$Ge rods were well resolved from their neighbors.

Figure 16:
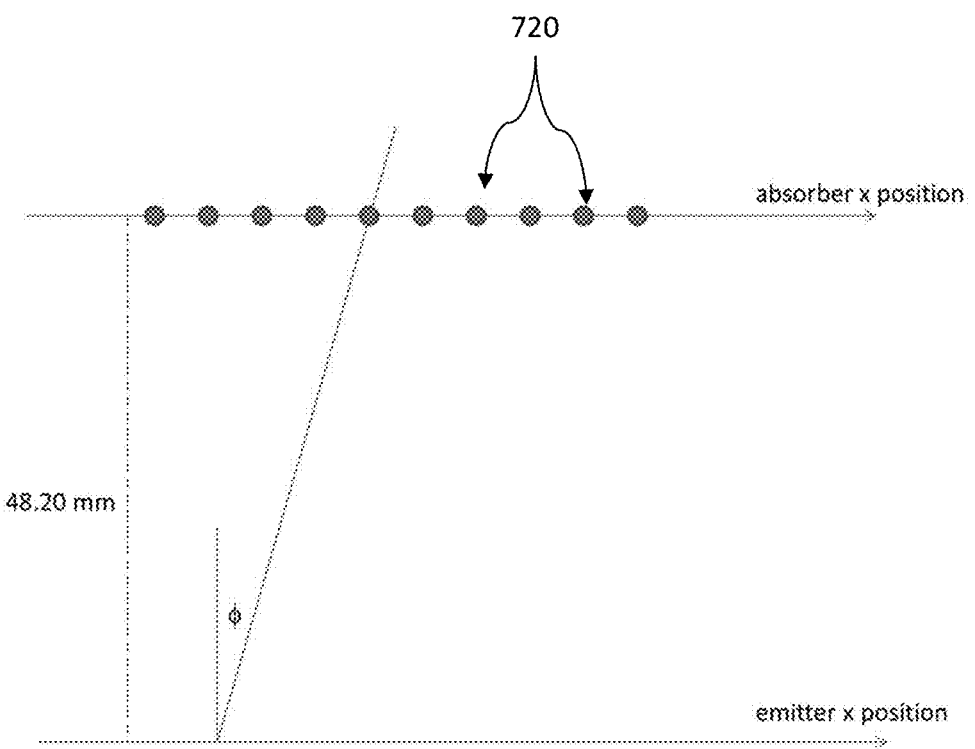
FIG. 16 is a schematic illustration of the positions of the $^{68}$Ge radiation source rods and the radiation-attenuating tungsten rods used in an experiment conducted to verify the effects of anti-pinhole collimation according to the present disclosure.

Next, we performed a simple reconstruction based on our knowledge that the $^{68}$Ge rods 710 (the radiation emitters) were distributed on a horizontal line 48.20 mm below the tungsten anti-pinhole rods. FIG. 16 shows a schematic of this arrangement between the $^{68}$Ge rods and the tungsten rods 720.

The reconstruction started with an empty array representing the emitter axis. The array was called p(ix) where ix represented bins separated by 0.1 mm. For each tungsten rod in positions H1 to H10, we calculated an emitter x coordinate with the equation:

$$\text{emitter } x \text{ coordinate} = \text{absorber } x \text{ coordinate} - 48.20 \text{ mm} \times \tan(\phi) \quad \text{(EQ 2)}$$

Figure 17:
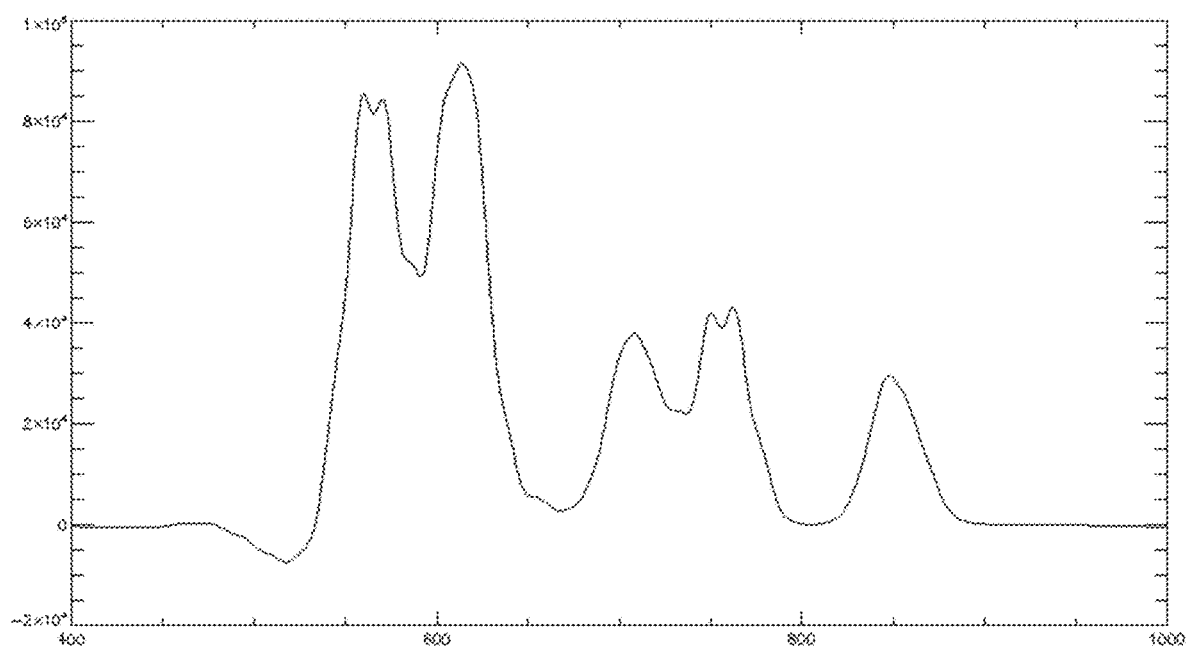
FIG. 17 is a plot of a projection data from reconstruction by the anti-pinhole collimation method.

We summed the sinogram fragments in FIG. 15C over several radial bins and incremented p(ix) by that amount. After applying (EQ 2) to each absorber rod, we smoothed p(ix) with a Gaussian kernel with 1.2 mm full width at half maximum (FWHM). This resulted in the projection graphed in FIG. 17. In FIG. 17, the x axis represents $\frac{1}{10}$ mm bins.

We estimated the resolution by analyzing the curve. Peaks clearly corresponded to the five radiation sources $^{68}$Ge rods. The peaks were in the expected positions and their heights were in proportion to the sources' known relative strengths. For comparison, a two-dimensional mathematical phantom was created that modeled the five radiation sources' positions and relative strengths. Starting with a delta-function model for these sources, two-dimensional Gaussian smoothing kernels of various FWHM were applied, and extracted one-dimensional profiles. This procedure resulted in the curves shown in FIG. 18. Successively lower profiles shown in the plot of FIG. 18 represent smoothing by 2 mm, 3.0 mm, 3.5 mm, and 4.0 mm, respectively.

In the model reconstruction (FIG. 17) and in the mathematical simulation (FIG. 18) the peak to valley ratios were extracted. These peak-to-valley ratios are provided in Table 2. We also considered peak to valley ratios based on normal PET, taking these values from FIG. 14.

TABLE 2

Figure 18:
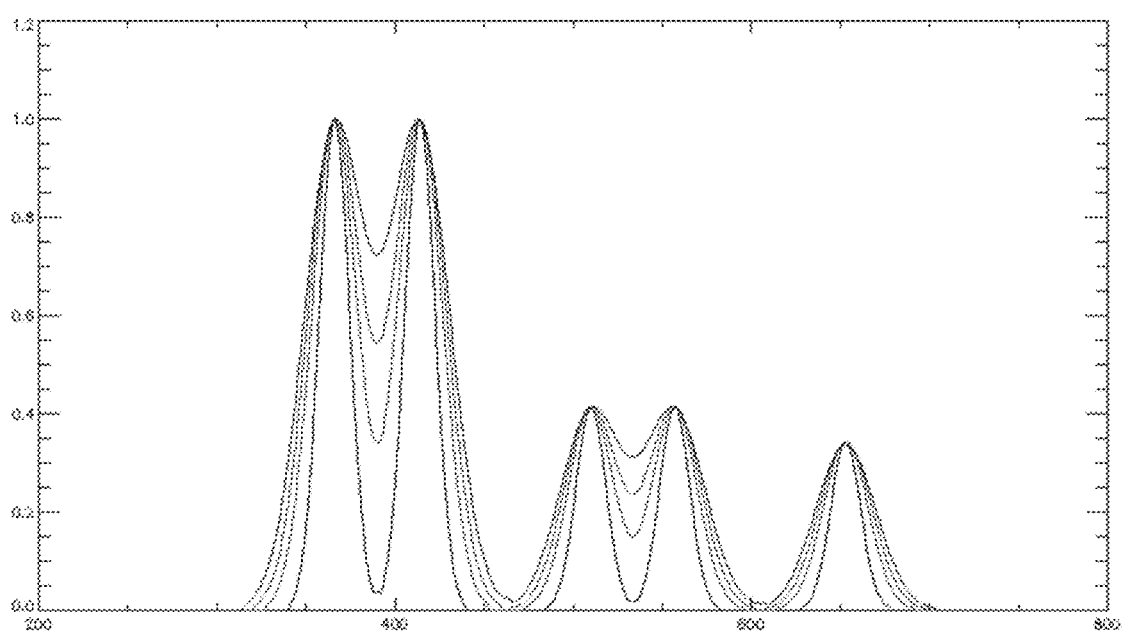
FIG. 18 shows a plot of profiles generated through mathematically modeled $^{68}$Ge rod phantoms.
Figure 19:
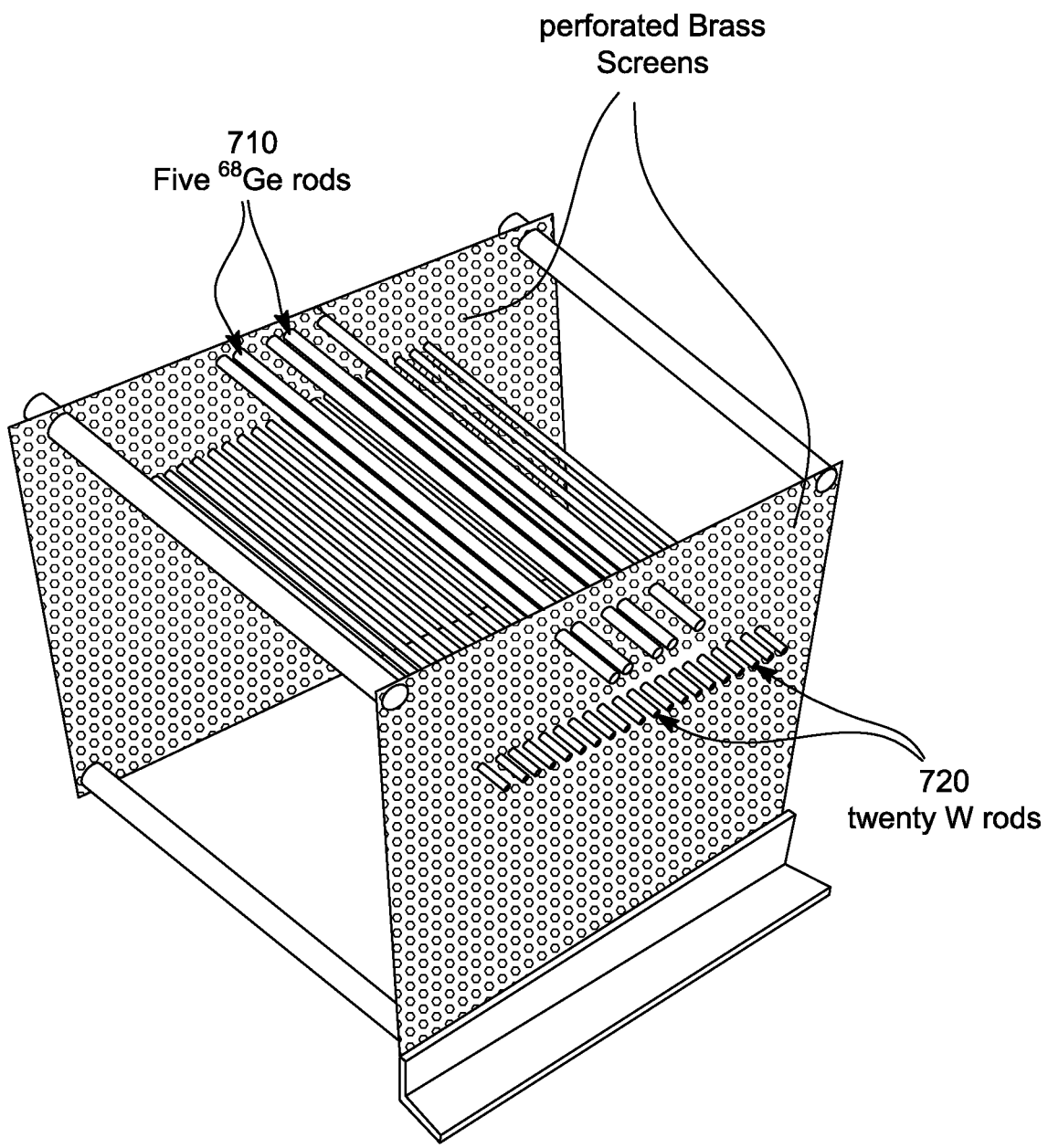
FIG. 19 is a photograph showing the experimental setup used to verify the anti-pinhole collimation effect of a plurality of radiation-attenuating rods in a parallel arrangement according to an embodiment of the present disclosure.

| Peak to valley ratios | |
|---|---|
| | Peak to Valley ratio |
| FIG. 18 anti-pinhole experiment, C1-C2 | 1.7 |
| FIG. 18 anti-pinhole experiment, C3-C4 | 1.8 |
| FIG. 15, normal PET, C1-C2 | 1.3 |
| FIG. 15, normal PET, C3-C4 | 1.3 |
| FIG. 19 simulation, C1-C2, 2 mm smoothing | 24.9 |
| FIG. 19 simulation, C1-C2, 3.0 mm smoothing | 2.92 |
| FIG. 19 simulation, C1-C2, 3.5 mm smoothing | 1.83 |
| FIG. 19 simulation, C1-C2, 4.0 mm smoothing | 1.37 |

The comparison suggested that the equivalent resolution in the anti-pinhole PET image and the normal PET image were approximately $$\text{experimental image resolution (anti-pinhole PET)} \cong 3.5 \text{ mm, and} \quad \text{(EQ 3)}$$

$$\text{experimental image resolution (normal PET)} \cong 4 \text{ mm.} \quad \text{(EQ 4)}$$

These resolution estimates do not reflect the resolution of the two approaches, anti-pinhole PET and normal PET. The addition-of-variances principle suggests that other effects could be included in quadrature according to the following equation:

$$(\text{image resolution})^2 = (\text{inherent resolution})^2 + (\text{degrading effects})^2. \quad \text{(EQ 5)}$$

Positron range within the $^{68}$Ge rod sources would degrade resolution in anti-pinhole PET and normal PET, causing a degrading effect with 1.8 mm FWHM. If we assumed that this was the main effect and solved (EQ 5) for inherent resolution, we would conclude as follows:

$$\text{inherent resolution (anti-pinhole PET)} \cong 3.0 \text{ mm,} \quad \text{(EQ 6)}$$

$$\text{inherent resolution (normal PET)} \cong 3.6 \text{ mm.} \quad \text{(EQ 7)}$$

The inventor believes that carefully performed resolution measurements with low-energy positrons might yield resolution values given by (EQ 6) and (EQ 7), in the case of a Biograph Horizon scanner.

Regarding the sensitivity of the anti-pinhole collimation, the net-true value in sinogram headers were used to estimate how much radiation was in effect absorbed by interposing the twenty tungsten rods. The totals could be affected by scattered radiation. See Table 3.

TABLE 3

| Sinogram totals | | |
| --- | --- | --- |
| | 5-rods phantom | mini Derenzo phantom |
| sinogram total without tungsten rods | 2.11E+08 | 4.27E+08 |
| sinogram total with tungsten rods | 1.82E+08 | 3.97E+08 |
| absorbed fraction | 13.8% | 7.0% |

This indicates that the anti-pinhole sensitivity was 7 to 14% of the sensitivity of a normal PET scan.

FIG. 19 is a photograph showing the experimental setup used to verify the anti-pinhole collimation effect of a plurality of radiation-attenuating rods in a parallel arrangement according to an embodiment of the present disclosure. The setup comprised of five $^{68}$Ge rods 710 as the gamma radiation source and twenty tungsten rods 720 in parallel arrangement as the radiation-attenuating rods simulating an anti-pinhole collimation unit. A grid of regularly spaced x-y positions for the rods were established using two approximately parallel perforated brass screens in which holes with diameter 0.138 inch (3.505 mm) were separated horizontally and vertically by 0.188 inch (4.775 mm). The screens were oriented transaxially and were about 150 mm apart.

Figure 20:
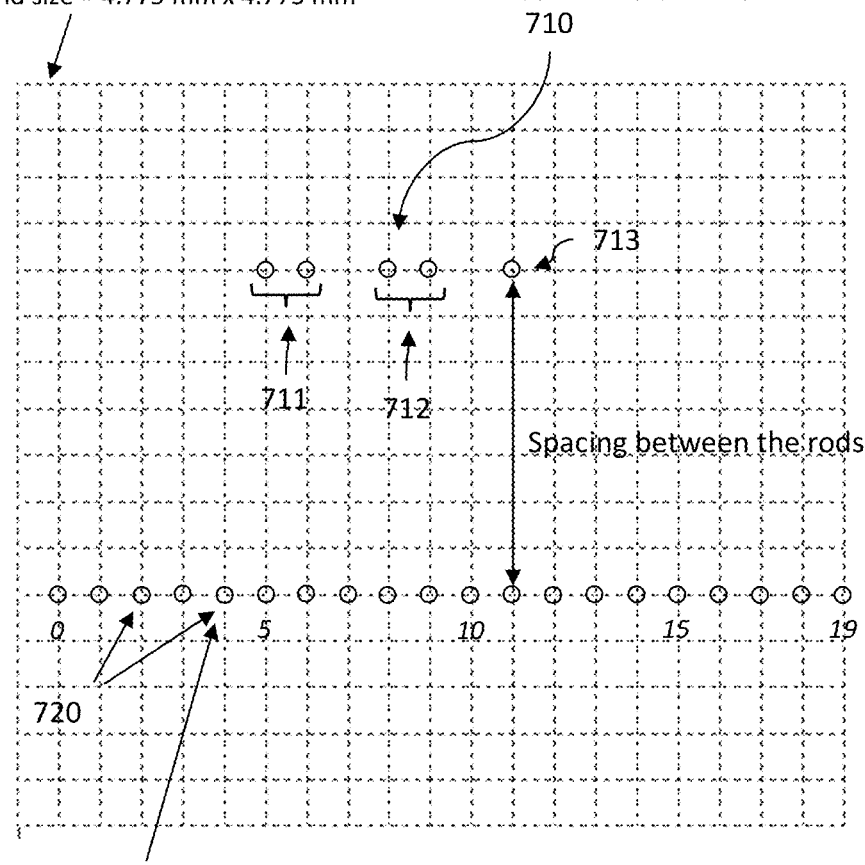
FIG. 20 is a schematic illustration of the plurality of radiation-attenuating rods in the parallel arrangement in the experimental setup shown in FIG. 19.

The tungsten rods 720 were positioned below the $^{68}$Ge rods. FIG. 20 is a schematic illustration of the end view of the $^{68}$Ge rods and the tungsten rods in the experimental setup of FIG. 19 showing the dimensions of the spacing between the rods. The five $^{68}$Ge rods were arranged into two pairs of $^{68}$Ge rods 711 and 712 and a single $^{68}$Ge rod 713. The $^{68}$Ge rods in each pair were spaced 4.775 mm apart, measured center-to-center, which was expected to be unresolvable in normal PET scans. The spacing between the two pairs 711, 712 and the spacing between the second pair 712 and the single $^{68}$Ge rod 713 were 2×4.775 mm, measured center-to-center, and this wider separation was expected to be well resolved in a normal PET scan. The twenty tungsten rods 720 were arranged parallel to each other and equally spaced at 4.775 mm apart, center-to-center.

Figure 21A:
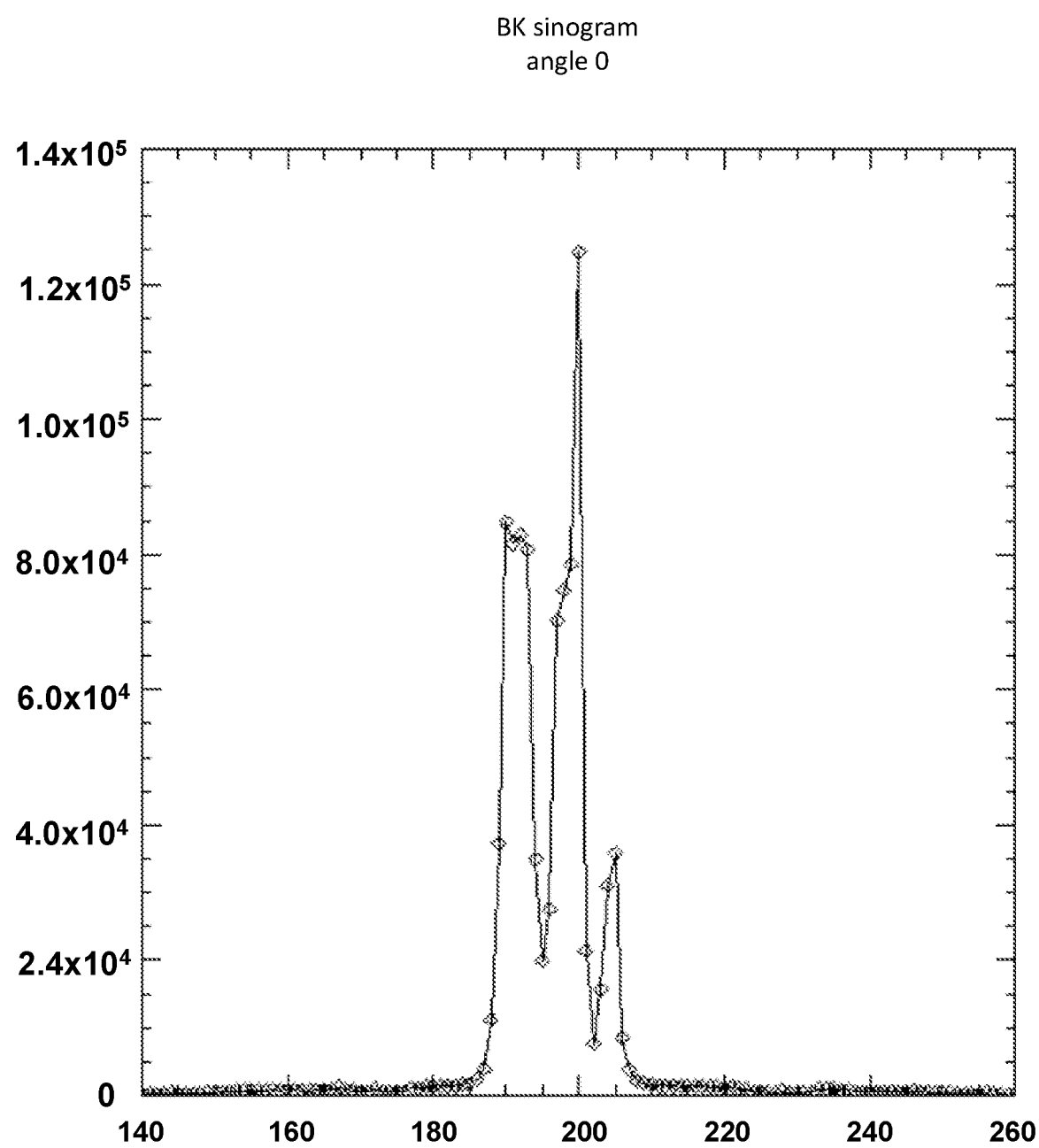
FIGS. 21A, 21B, and 21C are qualitative illustration of image reconstruction by projection of sinogram values onto the axis where the five $^{68}$Ge rods were located.
Figure 21B:
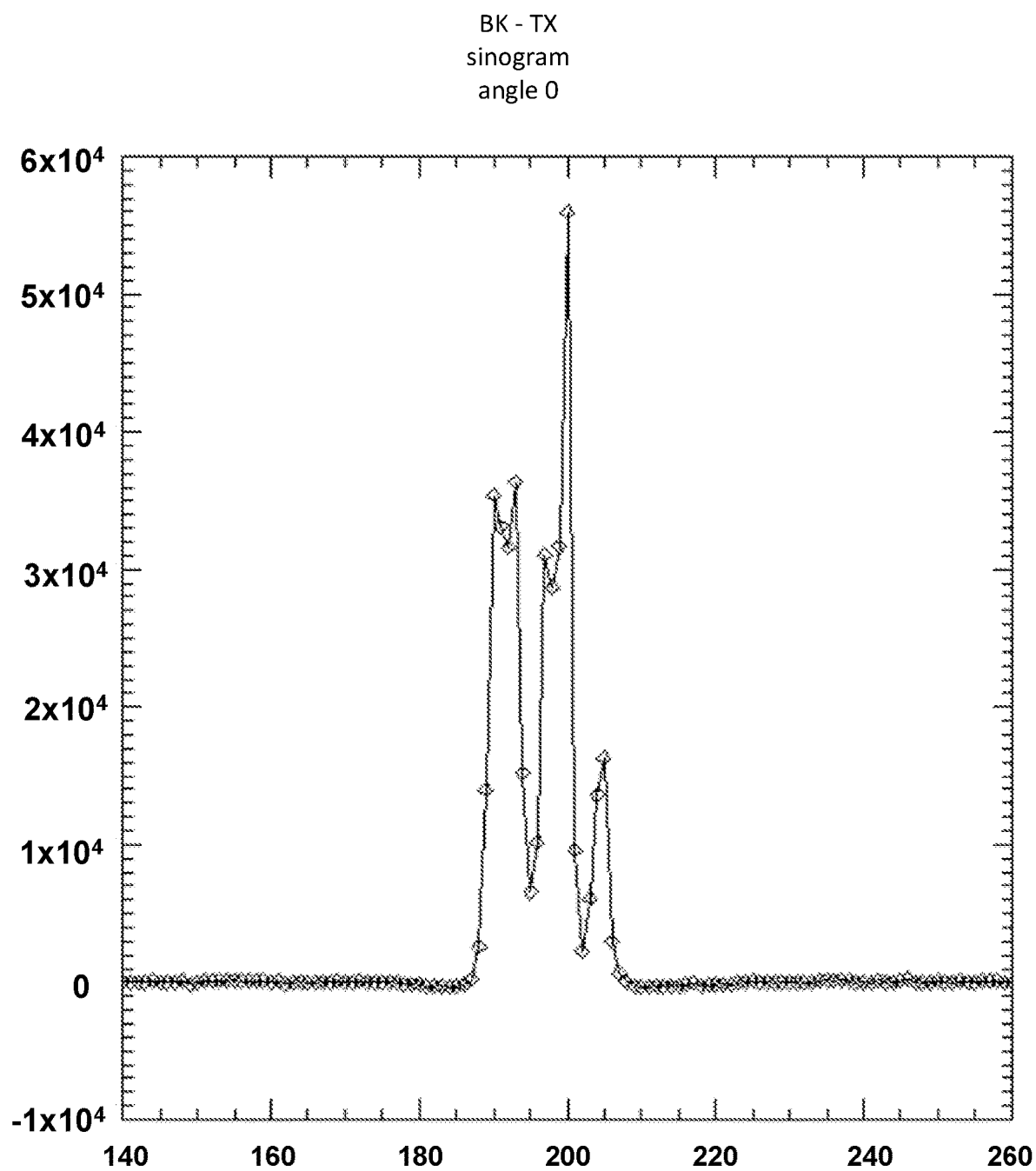
Figure 21C:
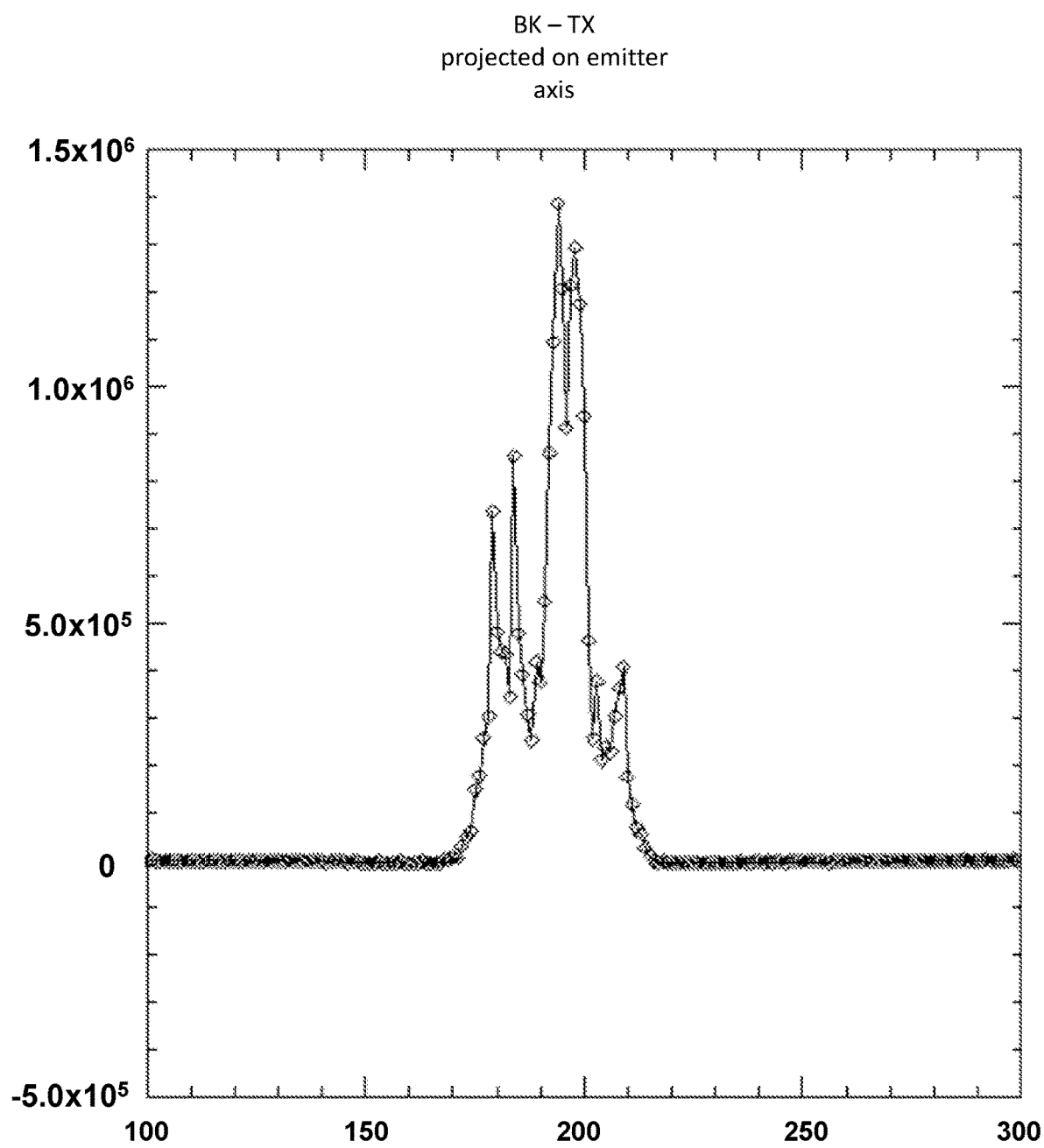

FIGS. 21A, 21B, and 21C are qualitative illustration of image reconstruction by projection of sinogram values onto the axis where the five $^{68}$Ge rods were located. In each plot, the horizontal axis is the position of the $^{68}$Ge rods in arbitrary units, and the vertical axis is the sum of sinogram values in arbitrary units. FIG. 21A is the projection of the sinogram values from a PET scan taken without the absorber rods 20. FIG. 21B is the projection of the sinogram values from a PET scan taken with the absorber rods 20. FIG. 21C is the projection of the difference between the sinogram values in FIG. 21A minus the sinogram values in FIG. 21B. The deep valleys between the peaks in FIG. 21C illustrate enhanced spatial resolution attributed to the anti-pinhole absorbers 20.

Although the subject matter has been described in terms of exemplary embodiments, it is not limited thereto. Rather, the appended claims should be construed broadly, to include other variants and embodiments, which may be made by those skilled in the art.

What is claimed is:

1. A method for imaging a region of interest in a patient using a positron emission tomography (PET) scanner comprising: (a) positioning a housing near the region of interest, wherein the housing is positioned closer to the region of interest than a detector associated with the PET scanner, wherein the housing is configured for holding a plurality of radiation-attenuating rods in a parallel arrangement such that when a plurality of radiation-attenuating rods are placed in the housing, all of the plurality of radiation-attenuating rods are in a first orientation with respect to the patient; (b) conducting a CT scan to obtain diagnostic information on the region of interest and for determining the location of the housing in the PET scanner's field of view; (c) placing a plurality of radiation-attenuating rods into the housing, wherein the plurality of radiation-attenuating rods are in the first orientation; (d) conducting one or more PET scans of the region of interest generating a projection data that includes the radiation-attenuating rods; and (e) reconstructing an image of the region of interest from the projection data.

2. The method of claim 1, wherein the first orientation is parallel to the patient's head-to-toe direction, front-to-back direction, or left-to-right direction.

3. The method of claim 1, further comprising a step of identifying the region of interest by X-ray topogram or camera scan before the step (a).

4. The method of claim 1, wherein the radiation-attenuating rods are made of a material that is one of tungsten, tantalum, thorium, lead, gold, stainless steel, or uranium.

5. The method of claim 4, wherein the diameter of the radiation-attenuating rods is less than two times the 511-keV photon attenuation length of the material.

6. The method of claim 4, wherein the radiation-attenuating rods are made of tungsten.

7. The method of claim 1, wherein the plurality of radiation-attenuating rods are spaced one diameter apart.

8. A method for imaging a region of interest in a patient using a positron emission tomography (PET) scanner comprising: (a) positioning a housing near the region of interest, wherein the housing is positioned closer to the region of interest than a detector associated with the PET scanner, wherein the housing is configured for holding a plurality of radiation-attenuating rods in a parallel arrangement such that when a plurality of radiation-attenuating rods are placed in the housing, all of the plurality of radiation-attenuating rods are in a first orientation with respect to the patient; (b) conducting a CT scan to obtain diagnostic information on the region of interest and for determining the location of the housing in the PET scanner's field of view; (c) placing a plurality of radiation-attenuating rods into the housing, wherein the plurality of radiation-attenuating rods are in the first orientation; (d) conducting one or more PET scans of the region of interest generating a first projection data that includes the radiation-attenuating rods in the first orientation; and (e) re-orienting the housing so that the plurality of radiation-attenuating rods are in a second orientation with respect to the patient; (f) conducting one or more PET scans of the region of interest generating a second projection data that includes the radiation-attenuating rods in the second orientation; and (g) reconstructing an image of the region of interest from the first and second projection data.

9. The method of claim 8, wherein the first orientation is a direction that is parallel to the patient's head-to-toe direction, front-to-back direction, or left-to-right direction;
the second orientation is also parallel to the patient's head-to-toe direction, front-to-back direction, or left-to-right direction; and
the first orientation and the second orientation are different.

10. The method of claim 8, further comprising a step of identifying the region of interest by X-ray topogram or camera scan before the step (a).

11. The method of claim 8, wherein the radiation-attenuating rods are made of a material that is one of tungsten, tantalum, thorium, lead, gold, stainless steel, or uranium.

12. The method of claim 11, wherein the diameter of the radiation-attenuating rods is less than two times the 511-keV photon attenuation length of the material.

13. The method of claim 11, wherein the radiation-attenuating rods are made of tungsten.

14. The method of claim 8, wherein the plurality of radiation-attenuating rods are spaced one diameter apart.

15. A method for imaging a region of interest in a patient using a positron emission tomography (PET) scanner comprising:
(a) positioning three housings near the region of interest, wherein each housing is configured to hold a plurality of radiation-attenuating rods in a parallel arrangement and the three housings are placed such that the plurality of radiation-attenuating rods in each of the three housings, when placed in the housings, are in a first, second, and third orientations with respect to the region of interest;
(b) conducting a CT scan to obtain diagnostic information on the region of interest and for determining the locations of the housings in the PET scanner's field of view;
(c) placing a plurality of radiation-attenuating rods into each of the three housings, wherein the plurality of radiation-attenuating rods in each of the three housings are in the first, second, and third orientations;
(d) conducting one or more PET scans of the region of interest generating a projection data that includes the radiation-attenuating rods in all three orientations; and
(e) reconstructing an image of the region of interest from the projection data.

16. The method of claim 15, wherein the first orientation is a direction that is parallel to the patient's head-to-toe direction, the second orientation is a direction that is parallel to the patient's front-to-back direction, and the third orientation is a direction that is parallel to the patient's left-to-right direction.

17. The method of claim 15, further comprising a step of identifying the region of interest by X-ray topogram or camera scan before the step (a).

18. The method of claim 15, wherein the radiation-attenuating rods are made of a material that is one of tungsten, tantalum, thorium, lead, gold, stainless steel, or uranium.

19. The method of claim 18, wherein the diameter of the radiation-attenuating rods is less than two times the 511-keV photon attenuation length of the material.

20. The method of claim 18, wherein the radiation-attenuating rods are made of tungsten.

21. The method of claim 15, wherein the plurality of radiation-attenuating rods are spaced one diameter apart.

22. A method for imaging a region of interest in a patient using a positron emission tomography (PET) scanner comprising:
(a) positioning three housings near the region of interest, wherein each housing is configured to hold a plurality of radiation-attenuating rods in a parallel arrangement and the three housings are placed such that the plurality of radiation-attenuating rods in each of the three housings, when placed in the housings, are in a first, second, and third orientations with respect to the region of interest;
(b) conducting a CT scan to obtain diagnostic information on the region of interest and for determining the locations of the housings in the PET scanner's field of view;
(c) conducting one or more PET scans of the region of interest generating a first projection data that does not include the radiation-attenuating rods;
(d) placing a plurality of radiation-attenuating rods into each of the three housings, wherein the plurality of radiation-attenuating rods in each of the three housings are in the first, second, and third orientations;
(e) conducting one or more PET scans of the region of interest generating a second projection data that includes the radiation-attenuating rods in the first, second, and third orientations; and
(f) reconstructing an image of the region of interest from the two projection data.

23. The method of claim 22, wherein the first orientation is a direction that is parallel to the patient's head-to-toe direction;
the second orientation is a direction that is parallel to the patient's front-to-back direction; and
the third orientation is a direction that is parallel to the patient's left-to-right axis.

24. The method of claim 22, further comprising a step of identifying the region of interest by X-ray topogram or camera scan before the step (a).

25. The method of claim 22, wherein the radiation-attenuating rods are made of a material that is one of tungsten, tantalum, thorium, lead, gold, stainless steel, or uranium.

26. The method of claim 25, wherein the diameter of the radiation-attenuating rods is less than two times the 511-keV photon attenuation length of the material.

27. The method of claim 25, wherein the radiation-attenuating rods are made of tungsten.

28. The method of claim 22, wherein the plurality of radiation-attenuating rods are spaced one diameter apart.

* * * * *